(12) United States Patent
Sessler et al.

(10) Patent No.: US 6,825,186 B1
(45) Date of Patent: Nov. 30, 2004

(54) METHOD AND COMPOSITIONS FOR TREATING ATHEROMA, TUMORS AND OTHER NEOPLASTIC TISSUE

(75) Inventors: Jonathan L. Sessler, Austin, TX (US); Darren Magda, Cupertino, CA (US)

(73) Assignees: Pharmacyclics, Inc., Sunnyvale, CA (US); Board of Regents, University of Texas System, Austin, TX (US)

( * ) Notice: Subject to any disclaimer, the term of this patent is extended or adjusted under 35 U.S.C. 154(b) by 220 days.

(21) Appl. No.: 09/699,027

(22) Filed: Oct. 27, 2000

Related U.S. Application Data

(60) Provisional application No. 60/287,588, filed on Oct. 29, 1999.

(51) Int. Cl.[7] .............................................. C07D 487/12
(52) U.S. Cl. ...................... 514/185; 540/472; 540/465; 540/145; 514/410
(58) Field of Search ................................ 514/185, 410; 540/472, 465, 145

(56) References Cited

U.S. PATENT DOCUMENTS

| | | | |
|---|---|---|---|
| 5,011,472 A | 4/1991 | Aebischer et al. ............. | 604/50 |
| 5,244,671 A | * 9/1993 | Vogel et al. ................. | 424/450 |
| 5,457,183 A | 10/1995 | Sessler et al. ................ | 534/11 |
| 5,599,928 A | 2/1997 | Hemmi et al. ............... | 540/474 |
| 5,622,946 A | 4/1997 | Sessler et al. ............... | 514/185 |
| 5,762,909 A | 6/1998 | Uzgiris ....................... | 424/9.34 |
| 5,776,925 A | 7/1998 | Young et al. ................ | 514/185 |
| 5,798,491 A | 8/1998 | Magda et al. .......... | 204/157.15 |
| 5,807,874 A | 9/1998 | LaVoie et al. ............... | 514/338 |
| 6,136,841 A | * 10/2000 | Platzek et al. .............. | 514/410 |

FOREIGN PATENT DOCUMENTS

| | | |
|---|---|---|
| EP | 0 786 253 A1 | 1/1997 |
| WO | WO 00/01414 | 1/2000 |

OTHER PUBLICATIONS

Lehninger, Biochemistry, 2nd Edition, pp. 640–643, Worth Publishers, 1975.*
Lehninger (Biochemistry, 2nd Edition, pp. 503–504; Worth Publishers, 1975).*
Kimoto, Cancer Research 43 (2) 824–8, 1983.*
Bram, Nature 284 (5757) 629–31, 1980.*
Adams et al., "Electron–Affinic Sensitization: VII. A Correlation between Structures, One–Electron Reduction Potentials, and Efficiencies of Nitroimidazoles as Hypoxic Cell Radiosensitizers," Radiation Research, vol. 67, pp. 9–20 (1976).
Buettner et al., "Catalytic Metals, Ascorbate and Free Radicals: Combinations to Avoid,"Radiation Research, vol. 145, pp. 532–541 (1996).
Chen et al., "A New Mammalian DNA Topoisomerase I Poison Hoechst 33342: Cytotoxicity and Drug Resistance in Human Cell Cultures," Cancer Research, vol. 53, pp. 1332–1337 (1993).
Harker et al., "Development and Characterization of a Human Sarcoma Cell Line, MES–SA, Sensitive to Multiple Drugs," Cancer Research, vol. 43, pp. 4943–4950 (1983).
Isoda et al., "Change in Ascorbate Radical Production in an Irradiated Experimental Tumor with Increased Tumor Size," Cancer Research, vol. 56, pp. 5741–5744 (1996).
Lin et al., "The Cytotoxic Activity of Hematoheme: Evidence for Two Different Mechanisms," Analytical Biochemistry, vol. 61, pp. 323–331 (1997).
Makhey et al. "Coralyne and Related Compounds as Mammalian Topoisomerase I and Topoisomerase II Poisons," Bioorganic & Medicinal Chemistry, vol. 4, No. 5, pp. 781–791 (1996).
Makhey et al., "Protoberberine Alkaloids and Related Compounds as Dual Inhibitors of Mammalian Topoisomerase I and II," Medical Chemistry Research, vol. 5, pp. 1–12 (1995).
Mosmann, "Rapid Colorimetric Assay for Cellular Growth and Survival: Application to Proliferation and Cytotoxicity Assays," Journal of Immunological Methods, vol. 65, pp. 55–63 (1983).
Riley, "Free Radicals in Biology: Oxidative Strees and the Effects of Ionizing Radiation," Int. J. Radiat. Biol., vol. 65, No. 1, pp. 27–33 (1994).
Rockwell et al., "Characteristics of a Serially Transplanted Mouse Mammary Tumor and Its Tissue–Culture–Adapted Derivative," Journal of the National Cancer Institute, vol. 49, No.3, pp. 735–749 (1972).
Sessler et al., "One–Electron Reduction and Oxidation Studies of the Radiation Sensitizer Gadolinium(III) Texaphyrin (PCI–0120) and Other Water Soluble Metallotexaphyrins," Journal of Physical Chemistry A, vol. 103, No. 7, pp. 787–794 (1999).
Sessler et al., "Texaphyrins: Synthesis and Applications," American Chemical Society, vol. 27, No. 2, pp. 43–50 (1994).
Young et al., "Preclinical Evaluation of Gadolinium(III) Texaphyrin Complex: A New Paramagnetic Contrast Agent for Magnetic Resonance Imaging," Investigative Radiology, vol. 29, No. 3, pp. 330–338 (1994).

* cited by examiner

Primary Examiner—Jon P. Weber
Assistant Examiner—David Lukton
(74) Attorney, Agent, or Firm—Vinit G. Kathardekar

(57) ABSTRACT

The radiation sensitization potential of a candidate compound can be screened by determine its ability to generate one or more reactive oxygen species under appropriate conditions. Compounds determined to have radiation sensitization potential are employed in methods for treating atheroma, tumors and other neoplastic tissue as well as other conditions that typically responsive to radiation sensitization.

5 Claims, 20 Drawing Sheets

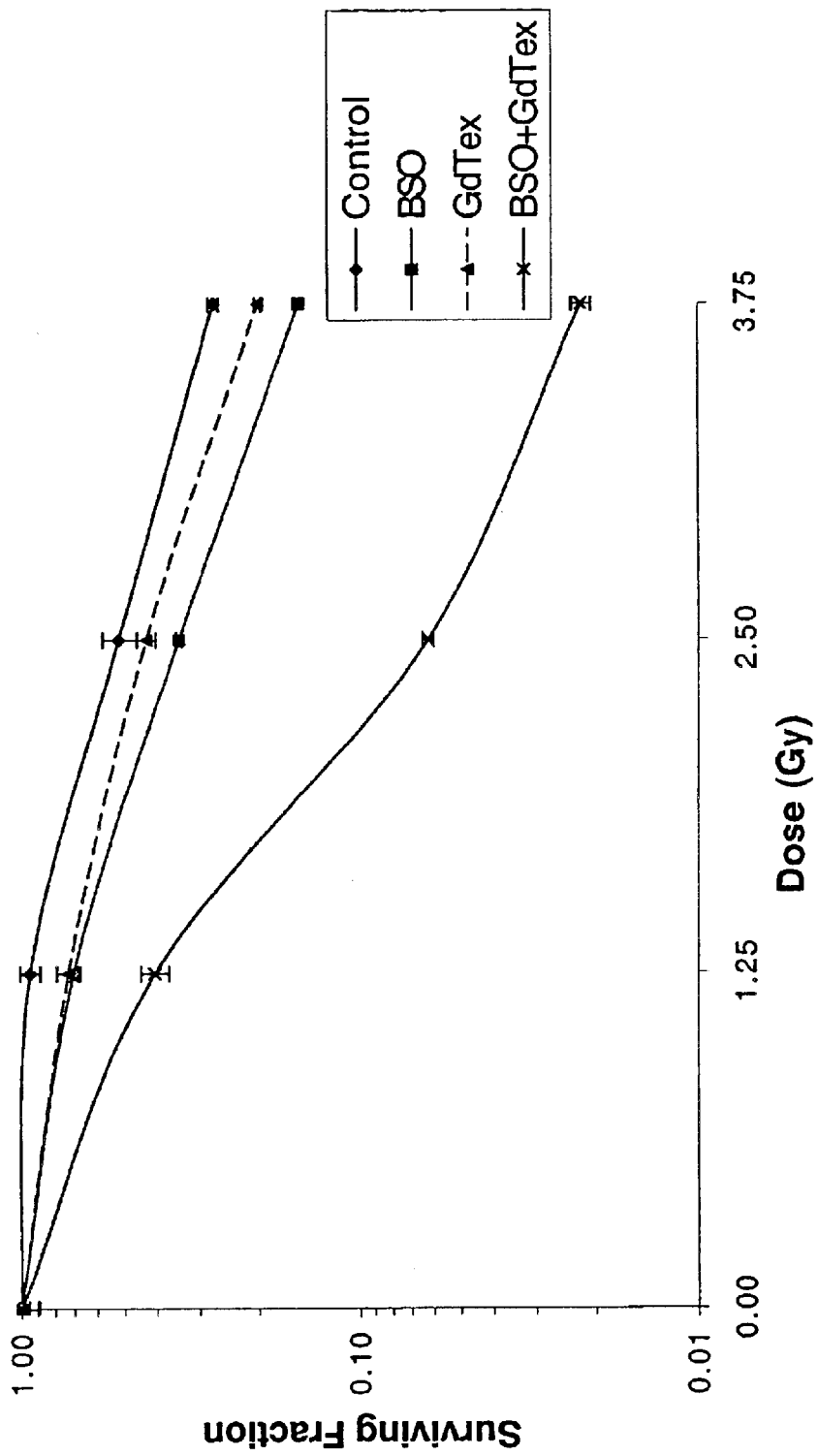
Fig. 18 MES-SA /McCoys 5A

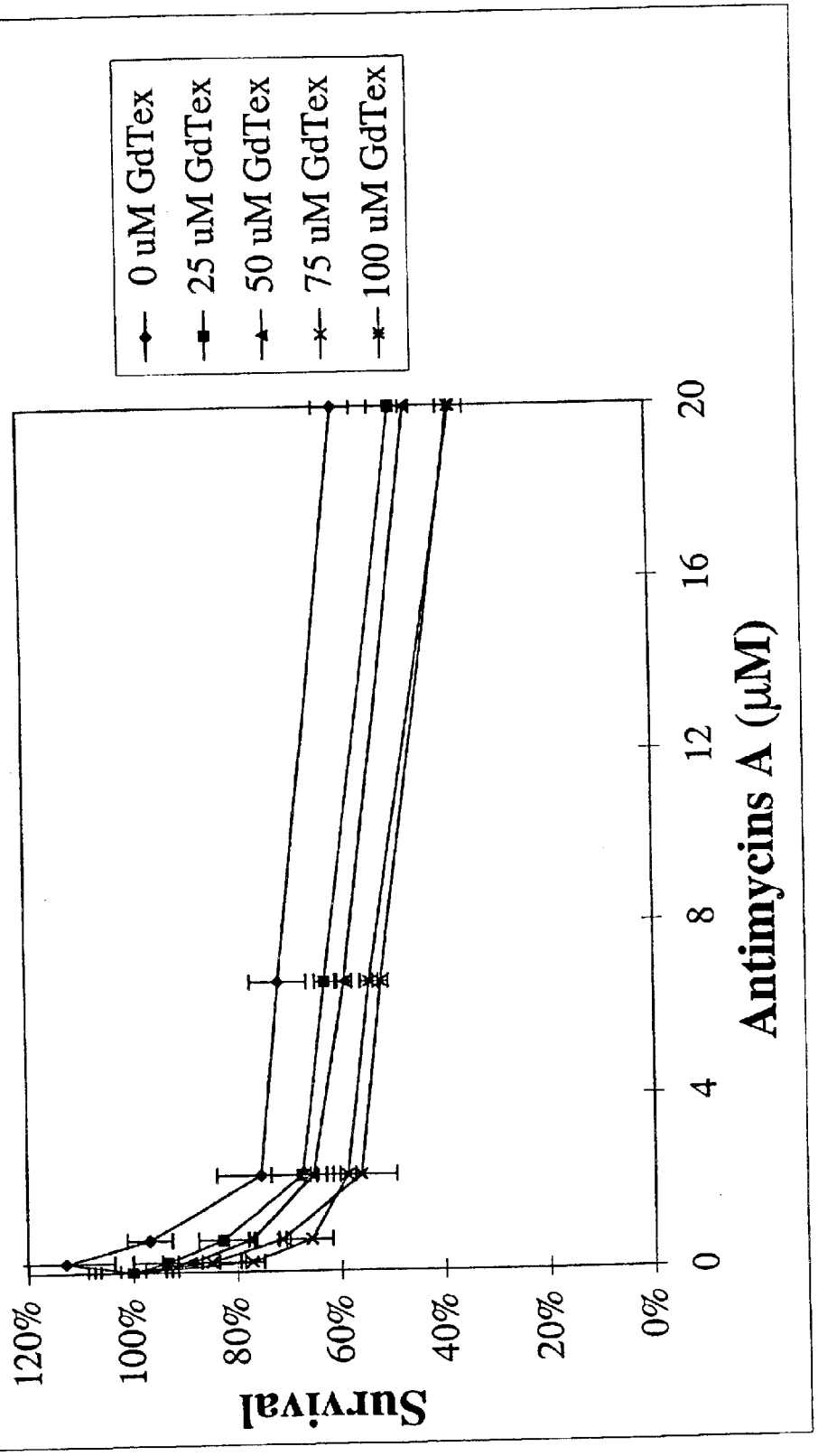
Fig. 19 BSO/Antimycins A/GdTex

METHOD AND COMPOSITIONS FOR TREATING ATHEROMA, TUMORS AND OTHER NEOPLASTIC TISSUE

CROSS-REFERENCE TO RELATED APPLICATIONS

This is a continuation-in-part of U.S. patent application Ser. No. 09/430,505 filed Oct. 29, 1999, now abandoned converted to provisional U.S. Patent Application Ser. No. 60/287,588, filed Oct. 29, 1999, incorporated herein by reference.

BACKGROUND OF THE INVENTION

1. Field of the Invention

This invention relates to novel methods and pharmaceutical formulations for treating atheroma, tumors and other neoplastic tissue, as well as other conditions that are responsive to the induction of targeted oxidative stress. This invention also relates to novel methods for determining the radiation sensitization potential of a compound.

2. Publications Cited by Reference

Certain publications are cited in this application through the use of the following superscript numbers:

[1] Buettner, et al., Radiation Research, *Catalytic Metals, Ascorbate and Free Radicals: Combinations to Avoid*, 145:532–541 (1996)

[2] Isoda, et al., J. Cancer Research, *Change in Ascorbate Radical Production in an Irradiated Experimental Tumor with Increased Tumor Size*, 56:5741–5744 (1996)

[3] Riley, Int. J. Radiat. Biol., *Free Radical in biology: oxidative stress and the effects of ionizing radiation*, 65(1):27–33 (1994)

[4] Sessler, et al., J. Phys. Chem. A, *One-Electron Reduction and Oxidation Studies of the Radiations Sensitizer Gadolinium (III) Texaphyrin (PCI-120) and Other Water Soluble Metallotexaphyrins*, 103: 787–794 (1999)

[5] Adams, et al., Radiation Res., 67:9–20 (1976)

[6] Riley, Int. J. Radiat. Biol., *Free Radicals in Biology: Oxidative Stress and the Effects of Ionizing Radiation*, 65(1):27–33 (1994)

[7] Magda, et al., U.S. Pat. No. 5,798,491, *Multi-Mechanistic Chemical Cleavage Using Certain Metal Complexes*, issued Aug. 25, 1999

[8] Young, et al., U.S. Pat. No. 5,776,925, *Methods for Cancer Chemosensitization*, issued Jul. 7, 1998

[9] Sessler, et al., U.S. Pat. No. 5,622,946, *Radiation Sensitization Using Texaphyrins*, issued Apr. 22, 1997

[10] Sessler, et al., U.S. Pat. No. 5,457,183, *Hydroxylated Texaphyrins*, issued Oct. 10, 1995

[11] Sessler, et al., Accounts of Chem. Res., *Texaphyrins: Synthesis and Applications*, 27:43–50 (1994)

[12] Hemmi, et al., U.S. Pat. No. 5,599,928, *Texaphyrin Compounds Having Improved Functionalization*, issued Feb. 4, 1997

[13] Young, et al., Investigative Radiology, 29:330–338 (1994)

[14] Mosmann, J. Immunol. Methods, 65:55–63 (1983)

[15] Lin, et al., Analytical Biochemistry, *The Cytotoxic Activity of Hematoheme: Evidence for Two Different Mechanisms*, 161:323–331 (1987)

[16] Volpin, et al., WO097/03666, EP 0 786 253 A1, U.S. Pat. No. 6,004,953, *Agent for Suppressing Tumor Growth*

All of the above publications are herein incorporated by reference in their entirety to the same extent as if each individual publication was specifically and individually indicated to be incorporated by reference in its entirety.

3. Background Information

The treatment of solid mammalian tumors with Ionizing radiation involves the in situ generation of hydroxyl radicals and other reactive oxygen species which, due to the focusability of the ionizing radiation are primarily located in the tumor, i.e., in tumor cells. These reactive species possess extreme oxidizing properties which oxidize biomolecules in vivo thereby interfering with cellular metabolism.[1] For example, it is reported that ionizing radiation, such as X-rays and γ-rays, induces irreversible damage to cellular DNA through production of hydroxyl radicals and other reactive oxygen species in the cell leading to cell death[2,3] or initiation of the mechanism of apoptosis.[4]

One generally accepted mechanism of the cellular effect of ionizing radiation is initial damage inflicted to the cell's DNA by reactive oxygen species generated by the ionizing radiation. In the presence of molecular oxygen, this damage is largely irreparable. Contrarily, in the absence of molecular oxygen (such as hypoxic cells), cellular antioxidants such as ascorbate and NAD(P)H can act to repair damage to the tumor DNA.

Tumor treatment via the use of ionizing radiation can be enhanced by increasing the radiosensitivity of the tumor cells. One method suggested for enhancing radiosensitivity has been the external administration of a compound having a high affinity for electrons, which ideally localizes in the tumor. Proposed radiation sensitizers include compounds such as halogenated pyrimidines, nitroimidazoles and gadolinium (III) complexes of the pentadentate macrocycle texaphyrin.[4] Motexafon gadolinium (a gadolinium (III) texaphyrin complex) is currently in Phase III clinical trials for the treatment of brain metastases.[4]

Phthalocyanine and naphthalocyanine polydentate ligands of the transition metals cobalt and iron have been described as suppressing the growth of tumor cells when administered in combination with a biogenic reductant such as ascorbic acid.[16]

The observation that radiation sensitization occurs as a function of redox potential gave rise to the proposal that such compounds function by interception of aqueous electrons, thus preventing their recombination with cytotoxic radicals.[5] Subsequent evidence showing a lack of radiation sensitization activity for lutetium (III) texaphyrin in animal models notwithstanding the rapidity of reaction between this complex and hydroxyl radicals under pulsed radiolytic conditions and minimal apparent nuclear localization suggest that this proposal might not fully explain the mechanism by which the gadolinium texaphyrins act as radiosenstizers.[4]

In view of the above, an understanding of the mechanism for radiosentization of tumor cells would be particularly helpful. Such an understanding could be used for testing in the discovery of new compounds useful as radiation sensitizers as well as in maximizing the therapeutic effect achieved by use of such compounds in the presence or the absense of ionizing radiation.

SUMMARY OF THE INVENTION

This invention is premised upon the unexpected observation that the known motexafin gadolium radiation sensitizer acts to catalyze the oxidation of NAD(P)H, ascorbate and other reducing agents under approximate physiological conditions, leading to reactive oxygen species generation. Depletion of these reducing agents will inhibit biochemical pathways that in vivo utilize reducing agents to effect repair of the damage inflicted by reactive oxygen species. Additionally, since hydrogen peroxide is recognized as probably the most significant of the reactive oxygen species[6], the generation of hydrogen peroxide will facilitate oxidative attack on the tumor or other tissue where it is produced.

Moreover, this discovery that motexafin gadolium acts to catalyze the oxidation of reducing agents under approximate physiological conditions to produce one or more reactive oxygen species such as superoxide and hydrogen peroxide, serves as a basis to assess the radiation sensitizing potential of other compounds. Specifically, a candidate compound can be screened to determine its ability to generate one or more reactive oxygen species under appropriate conditions. In turn, the amount of reactive oxygen species so produced is then correlated to the radiation sensitizing ability of the compound. Accordingly, in one of its method aspects, this invention is directed to a method for determining the radiation sensitization potential of a compound by the steps of:

a) introducing a compound to be tested into an aqueous solution of a cellular metabolite having a standard biochemical reduction potential more negative than the standard biochemical reduction of oxygen/hydrogen peroxide;

b) monitoring the solution for the occurrence of a reaction that produces one or more reactive oxygen species; and c) determining whether the compound has potential radiation sensitization activity, wherein the potential for radiation sensitization activity correlates to the occurrence of a reaction that produces one or more reactive oxygen species.

The reaction that produces a reactive oxygen species can be monitored in numerous manners as is well known to the skilled artisan, by measuring one or more of: depletion of oxygen, production of hydrogen peroxide, decreased concentration of the cellular metabolite, or generation of an oxidation product of the cellular metabolite. The cellular metabolite is preferably a compound selected from the group consisting of ascorbate, NADPH, NADH, $FADH_2$ and reduced glutathione. Even more preferably, the cellular metabolite is ascorbate or NADPH.

In another embodiment, a compound which is determined to have radiation sensitization potential by a method of the present invention can be administered to a mammalian host bearing a tumor and the tumor is subsequently exposed to ionizing radiation.

In still another embodiment there is provided a method for killing a tumor cells by:

a) administering to the tumor cell a compound (other than a texaphyrin) that catalyzes the production of one or more reactive oxygen species from a cellular metabolite having a standard biochemical reduction potential more negative than the standard biochemical reduction of oxygen/hydrogen peroxide; and b) exposing the cell to ionizing radiation. Preferably, the compound preferentially accumulates in tumor cells, e.g., as do porphyrin derivatives. One preferred compound is Fe(III) porphyrin.

The knowledge that certain compounds exhibiting radiation sensitizing properties can catalytically effect the production of one or more reactive oxygen species from cellular metabolites having a biochemical reduction potential more negative than oxygen/hydrogen peroxide also serves as a basis for a method to enhance the rate of tumor cell death by co-administration of a thiol-depleting compound to the cell. Such a thiol-depleting compound will reduce the level of thiol reducing agents such as glutathione thereby removing essential components of the metabolic pathways for repairing the cellular damage generated by the reactive oxygen species.

Accordingly, in another of its method aspects, this invention is directed to a method for killing a tumor cell, which method comprises:

a) selecting a compound having radiation sensitization potential as per above;

b) administering said compound to the tumor cell; and c) co-administering to the tumor cell a thiol-depleting agent. Preferably, the radiation sensitizing compound selected in step a) above is a texaphyrin and the thiol-depleting agent is buthionine sulfoximine.

The above method has applicability in the treatment of cancer in a patient. When so applied, this invention provides for a method of treatment of cancer comprising administering to a patient suffering therewith an effective amount of a texaphyrin radiation sensitzer, an effective amount of a thiol-depleting agent, and an effective amount of ionizing radiation.

In yet another of its method aspects, this invention is directed to a method for killing a tumor cell, which method comprises:

a) administering to said cell a compound that catalyzes the production of one or more reactive oxygen species from a cellular metabolite having a standard biochemical reduction potential more negative than the standard biochemical reduction of oxygen/hydrogen peroxide; and b) co-administering to said cell a second agent selected from the group consisting of DNA alkylators, topoisomerase inhibitors, redox cycling agents, thiol-depleting agents, metabolic inhibitors, and mitochondrial inhibitors. Preferred DNA alkylators include carmustine. Preferred redox cycling agents include alloxan, phenazine methosulfate, menadione, copper/putrescine/pyridine, methylene blue, paraquat, doxorubicin, bleomycin, and ruthenium (II) tris-(1,10-phenanthroline-5,6-dione). Preferrred thiol-depleting agents include buthionine sulfoximine and diethyl maleate. Preferred metabolic inhibitors include folic acid analogs (e.g., methotrexate and trimetrexate), pyrimidine analogs (e.g., fluorouracil, floxuridine, cytarabine and azacitidine), and purine analogs and related inhibitors (e.g., mercaptopurine, thioguanine, pentostatin and fludarabine). Preferred mitochondrial inhibitors include oligomycin and antimycin A. In another preferred embodiment, this method for killing tumor cells includes the additional step of exposing the cell to ionizing radiation.

In another, but related aspect of the invention, a first agent selected from the group consisting of DNA alkylators, topoisomerase inhibitors, redox cycling agents, thiol-depleting agents, metabolic inhibitors, and mitochondrial inhibitors is co-administered with a second agent that catalyzes the production of one or more reactive oxygen species from a cellular metabolite having a standard biochemical reduction potential more negative than the standard biochemical reduction of oxygen/hydrogen peroxide, to a subject having a condition (other than a tumor or atheroma) typically treated with such first agent.

Still further, in another aspect of this invention, there is provided a method of selectively killing cells in a mammalian host bearing a tumor or atheroma, which method comprises:

a) administering to said mammalian host an agent that catalyzes the production of one or more reactive oxygen species from an intracellular reducing agent, preferably ascorbate or NAD(P)H;

b) optionally, allowing sufficient time for said agent to preferentially accumulate in the cells of the tumor or atheroma; and c) administering to said mammalian host a source or precursor of the reducing agent such as to increase the reactive oxygen species production in the tumor or atheroma.

In one preferred embodiment, this method further includes the steps of exposing the tumor or atheroma to ionizing radiation. In another preferred embodiment, the agent employed in this method is motexafin gadolium or motexafin lutetium or combinations thereof.

In yet another aspect of this invention, there is provided a method of treating a mammalian host bearing a tumor or an atheroma comprising administering to that host a therapeutically effective amount of a combination of motexafin gadolinium and motexafin lutetium and exposing the tumor or atheroma to ionizing radiation.

In one of its composition aspects, this invention is directed to pharmaceutical compositions for selectively killing cells in a host bearing a tumor or atheroma comprising a pharmaceutically acceptable carrier and an effective amount of an agent that catalyzes the production of one or more reactive oxygen species from an intracellular reducing agent provided that said agent is not a texaphyrin.

In another of its composition aspects, the invention encompasses an agent that preferentially accumulates in tumor or atheroma cells and catalyzes the production of one or more reactive oxygen species from a cellular metabolite having a standard biochemical reduction potential more negative than the standard biochemical reduction of oxygen/hydrogen peroxide, a source or precursor of the cellular metabolite, and a pharmaceutically acceptable excipient.

Still further, this invention provides for use of an agent that catalyzes the production of one or more reactive oxygen species from an intracellular reducing agent in the treatment of mammalian tumors or atheroma.

BRIEF DESCRIPTION OF THE DRAWINGS

FIG. 18 illustrates the clonogenic survival of MES-SA human uterine cells with ionizing radiation in the presence of GdTex and/or BSO.

FIG. 19 illustrates the percent survival of MES-SA human uterine cells treated with BSO followed by varying concentrations of GdTex and Antimycins A.

DETAILED DESCRIPTION OF THE INVENTION

Figure 1:
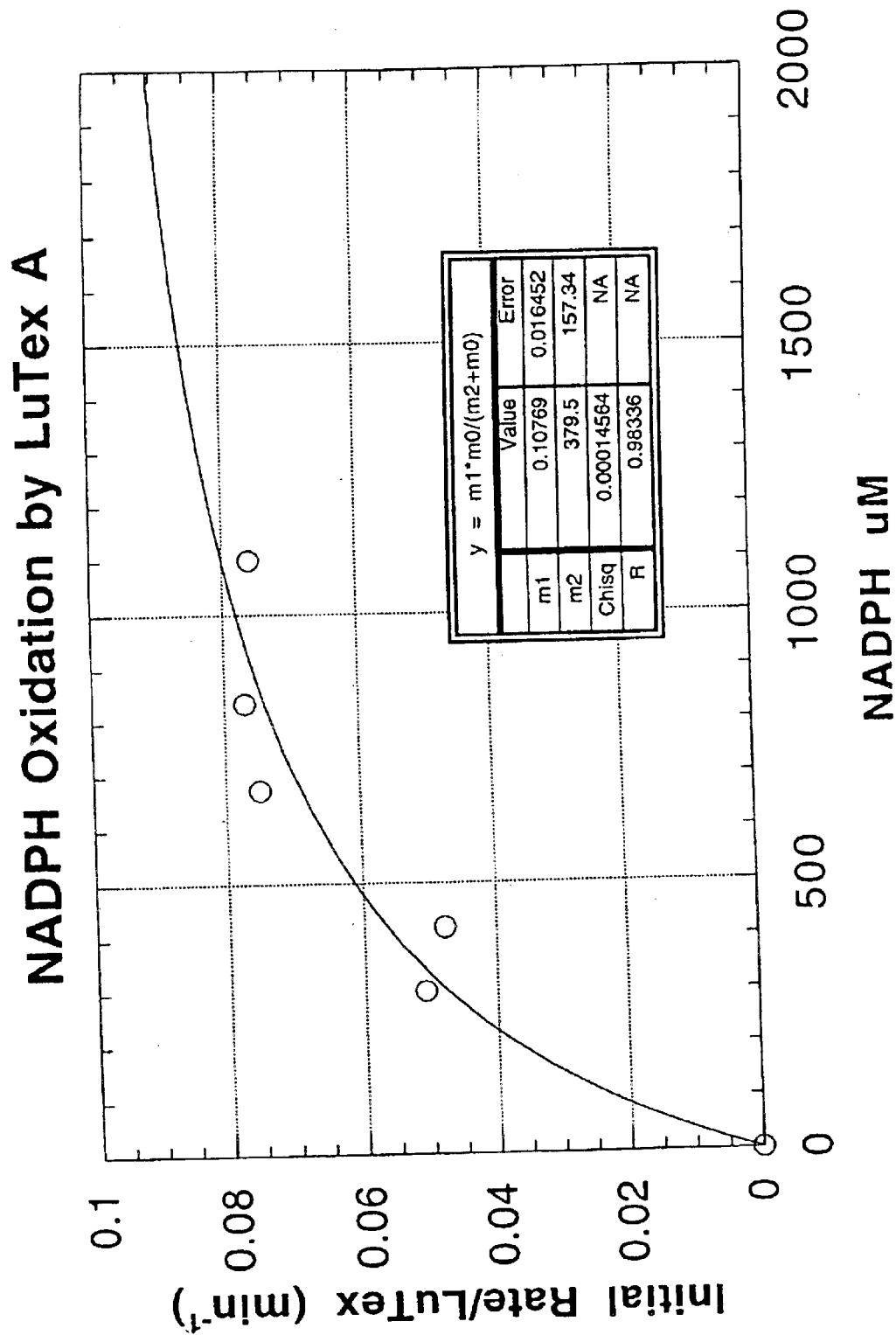
FIGS. 1-6 illustrate the rate of NADPH oxidation versus NADPH concentration by various metal cation complexes of a texaphyrin.

This invention is directed to novel methods for treating atheroma, tumors and other neoplastic tissue as well as other conditions that are responsive to the induction of targeted oxidative stress. However, prior to discussing this invention in further detail, the following terms will first be defined.

The term "texaphyrin" refers to aromatic pentadentate macrocyclic "expanded porphyrins" which are considered as being an aromatic benzannulene containing both 18 π and 22 π-electron delocalization pathways. Such texaphyrins and their synthesis are well known in the art.[7-12] Preferably, the texaphyrins encompass any and all texaphyrin compounds disclosed by Magda, et al.[7], Young, et al.[8], Sessier, et al.[9-11] and Hemmi, et al.[12]

Particularly preferred texaphyrins include those represented by formula I:

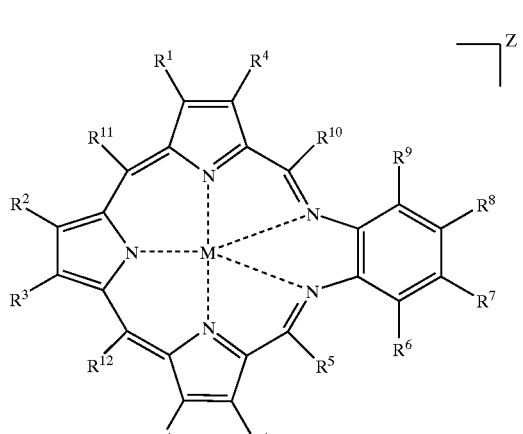

I wherein M is a divalent metal cation or a trivalent metal cation;

$R^1$ to $R^4$ as well as $R^7$ and $R^8$ are independently selected from the group consisting of hydrogen, carboxyl, carboxylalkyl, acyl, acylamino, aminoacyl, alkyl, substituted alky (particularly hydroxyalkyl or aminoalkyl, and especially where $R^1$ is hydroxypropyl or aminopropyl), alkenyl, substituted alkenyl, alkoxy, substituted alkoxy, aryl, heteroaryl, heterocyclic, halo, hydroxyl, nitro, and a saccharide;

$R^6$ and $R^9$ are independently selected from the group consisting of hydrogen, carboxyl, carboxylalkyl, acyl, acylamino, aminoacyl, alkyl, substituted alkyl other than iodoalkyl, alkenyl, substituted alkenyl, alkoxy, substituted alkoxy, aryl, heteroaryl, heterocyclic, halo other than iodo, hydroxyl, nitro, and a saccharide;

$R^5$ and $R^{10}$ to $R^{12}$ are independently selected from the group consisting of hydrogen, alkyl, substituted alkyl, alkoxy, substituted alkoxy, carboxyl, carboxylalkyl, acyl and acylamino; and the charge, Z, is an integer having a value less than or equal to 5.

The divalent or trivalent metal M is preferably selected from the group consisting of Ca(II), Mn(II), Co(II), Ni(II), Zn(II), Cd(II), Hg(II), Fe(II), Sm(II), $UO_2$(II), Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

Particularly preferred texaphyrin compounds are represented by formula II:

thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro,—SO-alkyl, —SO-substituted alkyl, —SO-aryl, —SO-heteroaryl, —$SO_2$-alkyl, —$SO_2$-substituted alkyl,—$SO_2$-aryl and —$SO_2$-heteroaryl.

The term "alkylene" refers to a diradical of a branched or unbranched saturated hydrocarbon chain, preferably having from 2 to 6 carbon atoms, more preferably 2 to 4 carbon atoms. This term is exemplified by groups such as ethylene (—$CH_2CH_2$—), the propylene isomers (e.g., —$CH_2CH_2CH_2$— and —$CH(CH_3)CH_2$—) and the like.

The term "substituted alkylene" refers to an alkylene group, as defined above, having from 1 to 5 substituents, and

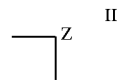

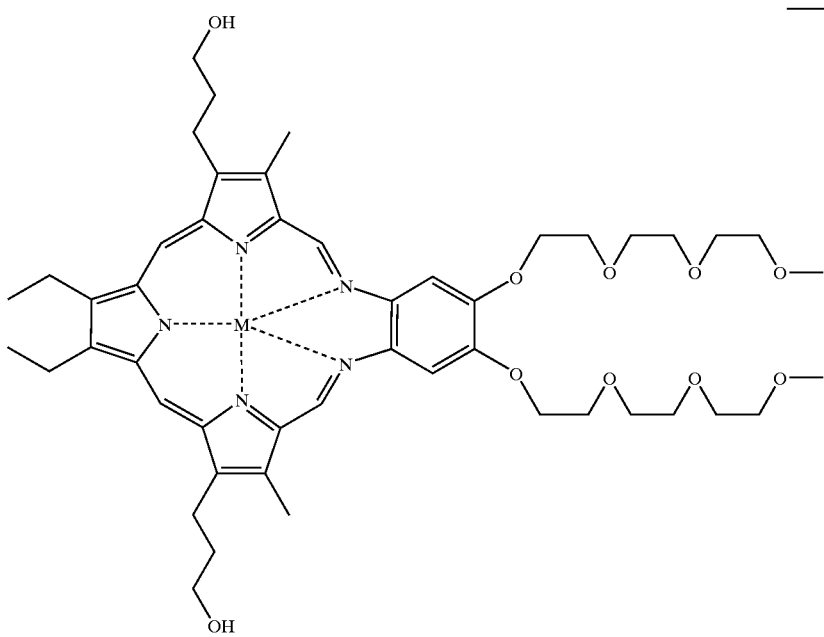

Even more preferred texaphyrin compounds are those of formula II wherein

A. M is Gd(III) and Z is +2;
B. M is Dy(III) and Z is +2;
C. M is Y(III) and Z is +2;
D. M is Lu(III) and Z is +2;
E. M is Co(II) and Z is +1;
F. M is Fe(III) and Z is +2;
G. M is Eu(III) and Z is +2;
H. M is Sm(III) and Z is +2;

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkoxy" refers to the groups alkyl-O—, alkenyl-O—, cycloalkyl-O— and cycloalkenyl-O—, where alkyl, alkenyl, cycloalkyl, and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—and substituted cycloalkenyl-O—, where substituted alkyl, substituted alkenyl, substituted cycloalkyl, and substituted cycloalkenyl are as defined herein. A preferred class of substituted alkoxy are polyoxyalkylene groups represented by the formula —O(R'O)$_q$R" where R' is an alkylene group or a substituted alkylene group, R' is selected from the group consisting of hydrogen, alkyl or substituted alkyl and q is an integer from 1 to 10. Preferably, in such groups, q is from 1 to 5 and most preferably 3.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)O—, substituted cycloalkyl-C(O)—, cycloalkenyl-C(O)—, substituted cycloalkenyl-C(O)—, aryl-C(O)—, heteroaryl-C(O)— and heterocyclic-C(O)—where alkyl, substituted alkyl, cycloalkyl, substituted cycloalkyl, cycloalkenyl, substituted cycloalkenyl, aryl, heteroaryl and heterocyclic are as defined herein.

The term "acylamino" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O—wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, cycloalkyl, cycloalkenyl, substituted alkyl, substituted alkoxy, substituted alkenyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O—wherein the aryl group is as defined above including optionally substituted aryl groups as also defined above.

The term "amino" refers to the group —NH$_2$.

The term "substituted amino refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, aryl, heteroaryl and heterocyclic provided that both R's are not hydrogen.

The term "carboxyalkyl" refers to the groups "—C(O)O-alkyl", "—C(O)O-substituted alkyl", "—C(O)O-cycloalkyl", "—C(O)O-substituted cycloalkyl", "—C(O)O-alkenyl", and "—C(O)O-substituted alkenyl", where alkyl, substituted alkyl, cycloalkyl, substituted cycloalkyl, alkenyl, and substituted alkenyl, are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro,—SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, cycloalkyl, cycloalkenyl, substituted alkyl, substituted alkoxy, substituted alkenyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or, multiple condensed rings (e.g., indolizinyl or benzothienyl). Preferred heteroaryls include pyridyl, pyrrolyl and furyl.

The term "heteroaryloxy" refers to the group heteroaryl-O—.

The term "heterocycle" or "heterocyclic" refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl,—SO-heteroaryl, —SO$_2$-alkyl, —SO,-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl—S- wherein the heteroaryl group is as defined above including optionally substituted aryl groups as also defined above.

The term "saccharide" refers to oxidized, reduced or substituted saccharides hexoses such as D-glucose, D-mannose, D-xylose, D-galactose, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as sucrose, lactose, or maltose; derivatives such as acetals, amines, acylated, sulfated and phosphorylated sugars; oligosaccharides having from 2 to 10 saccharide units. For the purposes of this definition, these saccharides are referenced using conventional three letter nomenclature and the saccharides can be either in their open or preferably in their pyranose form.

As to any of the above groups that contain one or more substituents, it is understood, of course, that such groups do not contain any substitution or substitution patterns which are sterically impractical and/or synthetically non-feasible. In addition, the compounds of this invention include all stereochemical isomers and mixtures thereof arising from the substitution of these compounds.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount" means a dosage sufficient to provide treatment for the disease state being treated. This will vary depending on the patient, the disease and the treatment being effected.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "cellular metabolite" or "reducing metabolite" refers to a compound found naturally within a living cell. The cellular metabolites employed to generate reactive oxygen species by the methods disclosed herein having a standard biochemical reduction potential more negative than the standard biochemical reduction potential of oxygen/hydrogen peroxide. Such metabolites include, by way of example only, NAD(P)H (i.e., NADPH and/or NADH), $FADH_2$, ascorbate, reduced glutathione, dihydrolipoic acid and the like.

The term "standard biochemical reduction potential" refers to the reduction potential of a metabolite measured at pH 7 and 25° C. in an aqueous solution. At these conditions, oxygen and hydrogen peroxide have a reduction potential of approximately 0.273 V.[16]

The term "thiol-depleting compound" refers to a compound which upon administration to a host or to a cell, results in a global lowering of the concentration of available reduced thiol (e.g., glutathione). Examples of thiol-depleting compounds include buthionine sulfoximine ("BSO", a known inhibitor of glutathione synthesis), diethyl maleate (a thiol reactive compound) dimethyl fumarate, N-ethyl maleimide, diamide (diazene dicarboxylic acid bis-(N,N'-dimethylamide)) and the like.

The term "ionizing radiation" refers to radiation conventionally employed in the treatment of tumors which radiation, either as a large single dosage or as repeated smaller dosages, will initiate ionization of water thereby forming reactive oxygen species. Ionizing radiation includes, by way of example, x-rays, electron beams, γ-rays, and the like.

The term "porphyrin derivative" refers to those molecules which contain as part of their chemical structure a polypyrrole macrocycle.

The term "DNA alkylators" refer to well known alkylating agents which alkylate DNA thereby interfering with cellular processes and leading to cell death. Suitable alkylating agents include nitrogen mustards (e.g., mechlorethamine, cyclophosphamide, ifosfamide, mephalan, chlorambucil and estramustine), etheleneimines and methylmelamines (e.g., hexamethylmelamine and thiotepa), alkyl sulfonates (e.g., busulfan), nitroureas (e.g., carmustine, lomusine, semustine, and streptozocin), and triazines (e.g., dacarbazine, procarbazine, and aziridine).

The term "topoisomerase" refers to enzymes that control and modify the topological states of DNA by catalyzing the concerted breaking and rejoining of DNA strands. (see, for example, D'Arpa et al., Biochim. Biophys. Acta, 989, 163 (1989). At least two distinct topoisomerases are known in the art and are designated as topoisomerase I and II.

The term "topoisomerase inhibitors" refers to compounds which in vivo inhibit one or more of the topoisomerase enzymes. Topoisomerase II inhibitors are well known in the art and include, by way of example, etoposide (VP-16), teniposide (VM-26), mitoxantrone, m-AMSA, adriamycin (doxorubicin), ellipticine and daunomycin. Topoisomerase I inhibitors are also well known in the art and include, for example, camptothecin and Hoechst 33342. See, for instance, Allan Y. Chen, et al., "A New Mammalian DNA Topoisomerase I Poison Hoechst 33342: Cytoxicity and Drug Resistance in Human Cell Cultures", Cancer Research, 53:1332–1337 (1993). Still other topoisomerase I and II inhibitors are disclosed in U.S. Pat. No. 5,807,874; by Darshan Makhey, et al., "Coralyne and Related Compounds as Mammalian Topoisomerase I and Topoisomerase II Poisons", Bioorg. & Med. Chem. Lett., 4:781–791, (1996) and Darshan Makhey, et al., "Protoberberine Alkaloids and Related Compounds as Dual Inhibitors of Mammalian Topoisomerase I and II", Med. Chem. Res., 5:1–12(1994). All of these references are incorporated herein by reference in their entirety.

The term "redox cycling agents" refers to compounds which may exist in two or more oxidation states and are able to lower the activation barrier for electron transfer between two compounds. Examples of suitable redox cycling agents include, for instance, alloxan, phenazine methosulfate, menadione, copper/putrescine/pyridine, methylene blue, paraquat, doxorubicin, bleomycin, and ruthenium (II) tris-(1,10-phenanthroline-5,6-dione).

The term "metabolic inhibitors" or "antimetabolites" refer to materials which interfere with the availability of one or more cellular metabolites such as ascorbate, NAD(P)H, etc. Such metabolic inhibitors are well known in the art and include, by way of example, folic acid analogs (e.g., methotrexate and trimetrexate), pyrimidine analogs (e.g., fluorouracil, floxuridine, cytarabine and azacitidine), and purine analogs and related inhibitors (e.g., mercaptopurine, thioguanine, pentostatin and fludarabine).

The term "mitochondrial inhibitors" refers to compounds that interfere with mitochondrial metabolism including, for example, oligomycin (a specific inhibitor of motochondrial ATP-ase, i.e., complex 5) and antimycins A (a complex 3 inhibitor that blocks the conversion of ubiquinol to ubiquinone).

Methods

Compounds that display affinity for electrons can potentiate the biological effect of ionizing radiation and, accordingly, may have use as radiation sensitizers. The determination of which compounds displaying electron affinity may possess radiation sensitization properties was heretofore not possible absent in vivo trial and error testing. Indeed, motexafin gadolinium [PCI-0120, Xcytrin™, GdTex, Formula II where M is Gd(III)] is reported to enhance the efficacy of radiation in animal tumor models and is currently in Phase III clinical development as an adjuvant to radiation therapy.[11,13] However, the related lutetium(III) congener (PCI-0123, Lutrin™, LuTex) in the same animal model did not possess similar radiation sensitization properties. These results have led us to explore the chemical mechanisms for the observed biological activity of GdTex.

Biochemically, two cellular forms of rapidly accessible energy are maintained for metabolic use: high energy phosphoryl linkages [e.g., phosphocreatine, ATP) and electron carriers, i.e., the cofactors NAD(P)H]. Initially, texaphyrins were evaluated for their ability to alter cellular energy charge by catalyzing the hydrolysis of high energy phosphoryl linkages. The results of this evaluation suggested some apparent effect; however, the observed rate accelerations seemed incompatible with biological importance.

Co-incubation of NADH or NADPH with texaphyrin derivatives, however, rapidly converted these cofactors to their oxidized forms, at catalytic concentrations of complex. Examination of texaphyrins containing different lanthanide ions showed that the observed oxidation rates measured by the amount of NADP+ formed correlated with Lewis acidity, whereas the transition metal derivatives displayed a lack of reactivity which is consistent with the fact that the redox potentials of texaphyrin complexes of divalent cations are about 200 mV more negative than those of the trivalent cations. It is also consistent with the lower attraction of oxygen anion ligands for transition metal cations than for lanthanide cations. The results of this examination are depicted in FIGS. 1-6.

Without being limited to any theory, these findings suggested that the reaction proceeded via initial complexation of cofactor phosphoric anhydride with the metal center, followed by slow two-electron (or hydride) transfer to the texaphyrin macrocycle. Indeed, the reaction displayed saturation kinetics.

The above studies were conducted under aerobic conditions. Replacement of oxygen with inert atmosphere led to rapid texaphyrin complex degradation, as evidenced by bleaching of the characteristic texaphyrin uv-vis absorbance spectrum (data not shown). Again, without being limited to any theory, this led to the supposition that oxygen might serve as the ultimate electron acceptor under aerobic conditions.

As illustrated in Examples 1–4 below, this supposition was assessed by measuring the formation of oxidized species or hydrogen peroxide upon incubation of the cellular metabolite NADPH with LuTex (Examples 1 and 3) or the cellular metabolite ascorbate with GdTex (Examples 2 and 4). As appropriate, the addition of catalase to the reaction mixture confirmed that the assay signal generated therein was due to hydrogen peroxide. In each case, the cellular metabolites, NADPH and ascorbate, have a standard biochemical reduction potential more negative than the standard biochemical reduction of oxygen/hydrogen peroxide.

These results evidenced that a compound's potential to exhibit radiation sensitizing activity correlates to its ability to form one or more reactive oxygen species from cellular metabolites which have a standard biochemical reduction potential more negative than the standard biochemical reduction of oxygen/hydrogen peroxide. In turn, this provides a facile method for testing a compounds radiation sensiziting capacity by introducing the to-be tested compound into an aqueous solution comprising a cellular metabolite having a standard biochemical reduction potential more negative than the standard biochemical reduction potential of oxygen/hydrogen peroxide; monitoring the solution for the occurrence of a reaction that produces one or more reactive oxygen species; and determining whether the compound has probable radiation sensitization activity, wherein this activity correlates to the occurrence and extent of a reaction that produces reactive oxygen species.

As is apparent, this assay can monitor any of a number of different components to assess the extent of the reaction. For example, the depletion of the cellular metabolite can be assayed; the production of an oxidized form of cellular metabolite can be assayed; the depletion of oxygen from the reaction solution can be assayed; or the appearance of hydrogen peroxide can be assayed. Each of these assays can, in turn, be used to determine the extent of reaction. As above, the cellular metabolite employed is one that has a standard biochemical reduction potential more negative than the standard biochemical reduction of oxygen/hydrogen peroxide. Such metabolites include, by way of example only, NADPH, NADH, FADH, ascorbate and reduced glutathione.

In a particularly preferred embodiment, compounds determined to have radiation sensitization activity by virtue of their ability to generate one or more reactive oxygen species in vivo are useful as adjuncts to treating mammalian tumors by ionizing radiation. In this embodiment, the compound possessing radiation sensitization activity is administered to the tumor in sufficient quantities to therapeutically enhance the effect of ionizing radiation on tumor cell death.

For example, the proliferation of human ovarian cancer cell line MES-SA[7] can be used to assess the degree of ascorbate and cofactor oxidation under cell culture conditions. RPMI 1640, which contains no ascorbate, was used as the medium in these experiments. Specifically, as illustrated in Examples 3 and 4, coincubation of ascorbate and GdTex or LuTex resulted in decreased cell proliferation, as measured by tetrazolium salt (MTT) reduction,[14] due to hydrogen peroxide formation. This occurred at concentrations of ascorbate, which parallel the dissociation constant values found. Similar results were obtained using NADPH as substrate.

Particularly useful radiation sensitizers are compounds that preferentially localize in the tumors. For example, it is well known that texaphyrin and porphyrin compounds will preferentially localize in mammalian tumors and have potential radiation sensitization activity. Similarly, other compounds determined to have radiation sensitization activity may also preferentially localize in mammalian tumors or such compounds can be derivatized to impart preferential localization in mammalian tumors. For example, such compounds can be derivatized by conventional synthetic chemical techniques to append to a molecule which is known to localize in mammalian tumors. Such molecules include monoclonal antibodies directed to tumor antigens, texaphyrins, porphyrins, peptides such as disclosed by Urzgiris, et al., U.S. Pat. No. 5,762,909 which is incorporated herein by reference in its entirety, etc. Specific techniques for coupling such compounds are disclosed in U.S. patent application Ser. No. 09/431,298, filed Oct.29, 1999 and entitled "Compounds for Treating Atheroma, Tumors and other Neoplastic Tissue" which application is incorporated herein by reference in its entirety.

One preferred compound for use as a radiation sensitizer are porphyrin derivatives and, in particular, iron(III) porphyrin. Such derivatives are known to accumulate in tumor tissue and iron(III) porphyrin has been disclosed as generating hydrogen peroxide from ascorbate and oxygen.[15]

Alternatively, the generation of one or more reactive oxygen species by the radiation sensitizers of the present invention can be used by itself (or in conjunction with the administration of a reducing metabolite) to therapeutically treat a tumor or atheroma. When used in conjunction with the administration of such reducing metabolites, the radiation sensitizers encompassed by the present invention exclude the cobalt and iron complexes of phthalocyanine and napthalocyanine. In one aspect of the invention, this can be particularly useful when the patient has been exposed to the maximum amount of ionizing radiation which can be tolerated by the patient.

Further, the role of glutathione and ascorbate towards lesions induced by ionizing radiation has been well studied.[11] it is generally accepted that a competition exists between these species and molecular oxygen for DNA lesions, such that a protective role for glutathione (and, at low levels of glutathione, ascorbate) can be demonstrated under anoxic conditions. As is known in the art, glutathione imparts a protective role by virtue of a redox reaction wherein the free thiol group of glutathione is oxidized to form a disulfide linkage with a second oxidized glutathione molecule. Accordingly, in order to limit the protection afforded by gluathione or other thiol containing antioxidants, this invention contemplates co-administraton of an effective amount of a thiol-depleting agent to the tumor cell or to a patient suffering from cancer in order to reduce the amount of thiol containing antioxidants contained therein. Preferably the thiol-depleting agent is buthionine sulfoximine.

Alternatively, known chemotherapeutic agents or other agents which alter metabolic pathways can be co-administered with the radiation sensitizing compound. Such agents include, by way of example, DNA alkylators, topoisomerase inhibitors, redox cycling agents, metabolic inhibitors and mitochondrial inhibitors.

Figure 15:
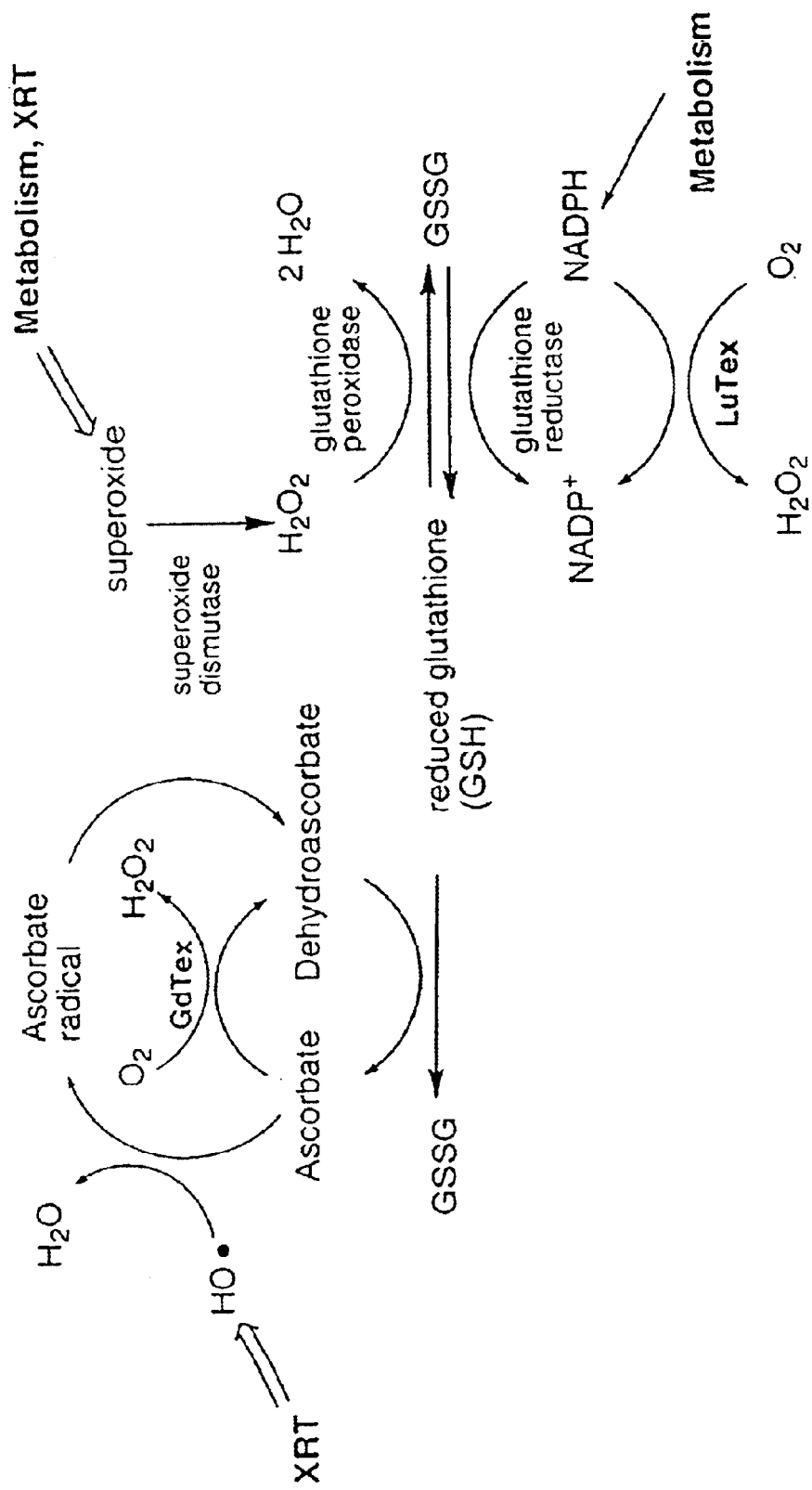
FIG. 15 illustrates a proposed mechanism to explain the production of reactive oxygen species by motexafin gadolinium and motexafin lutetium.

The metabolic balance of a cell entails numerous synchronous reactions. FIG. 15 illustrates pathways entailing the cellular metabolites ascorbate and NADPH, both of which have a standard biochemical reduction potential more negative than the standard biochemical reduction potential of oxygen/hydrogen peroxide. Agents capable of catalyzing the production of one or more reactive oxygen species from either or both of these cellular metabolites can drive the cell toward a state of oxidative stress. Also illustrated are certain of the effects of ionizing radiation, e.g., leading to the generation of hydroxyl radicals and additional hydrogen peroxide. Employing the methods of the present invention, it has been determined that motexafin gadolinium catalyzes the production of hydrogen peroxide from ascorbate to a much greater extent than does motexafin lutetium, whereas the converse is true with respect to NADPH. This suggests the co-administration of motexafin gadolinium and motexafin lutetium to drive both of these pathways as a means of increasing oxidative stress to increase a cell's sensitivity to radiation.

The preferred pharmaceutical compositions and methods of treatment of the present invention include the following:

Co-administration of a texaphyrin and a thiol-depleting agent, a reducing metabolite or source thereof, or a mitochondrial inhibitor, with or without ionizing radiation.

Co-administration of a texaphyrin and a thiol-depleting agent, with or without ionizing radiation; particularly where the thiol-depleting agent is BSO and most preferably with ionizing radiation. Especially preferred are the co-administration of a thiol-depleting agent with GdTex, CoTex, the mu-oxo dimer of iron texaphyrin ("Fe(Tex)$_2$O"), EuTex, SmTex, di-amino GdTex and di-amino LuTex, again, more preferably where the thiol-depleting agent is BSO and most preferably with ionizing radiation. The co-adminstration of GdTex and BSO, followed by administration of ionizing radiation, is most preferred.

Co-administration of a texaphyrin and a reducing metabolite or source thereof, with or without ionizing radiation, particularly where the texaphyrin is co-administered with ascorbate. Especially preferred are the co-administration of a reducing metabolite with GdTex, CoTex, the mu-oxo dimer of iron texaphyrin ("Fe(Tex)$_2$"), EuTex, SmTex, di-amino GdTex and di-amino LuTex, again, more preferably where the reducing metabolite is ascorbate and most preferably with ionizing radiation. The co-adminstration of GdTex and ascorbate, followed by administration of ionizing radiation, is most preferred.

Co-administration a texaphyrin (particularly GdTex), BSO and ascorbate, with or without ionizing radiation, and most preferably followed by ionizing radiation.

Co-administraton of a non-texaphyrin compound that catalyzes the production of one or more reactive oxygen species from a cellular metabolite having a standard biochemical reduction potential more negative than the standard biochemical reduction of oxygen/ hydrogen peroxide and ionizing radiation.

Co-administration of a DNA alkylator, thiol-depleting agent, topoisomerase inhibitor, redox cycling agent, metabolic inhibitor and/or mitochondrial inhibitor and a non-texaphyrin compound that catalyzes the production of one or more reactive oxygen species from a cellular metabolite having a standard biochemical reduction potential more negative than the standard biochemical reduction of oxygen/hydrogen peroxide, with or without ionizing radiation (excluding ascorbic acid with cobalt or iron phthalocyanines and naphthalocyanines without ionizing radiation).

Co-administration of a redox cycling agent and a non-texaphyrin compound that catalyzes the production of one or more reactive oxygen species from a cellular metabolite having a standard biochemical reduction potential more negative than the standard biochemical reduction of oxygen/hydrogen peroxide, with or without ionizing radiation, particularly where the redox cycling agent is doxorubicin or bleomycin, and most particularly with ionizing radiation. Especially preferred is the non-texaphyrin compound methylene blue, co-administered with bleomycin or doxorubicin, and without ionizing radiation.

Excluded from the pharmaceutical compositions and methods of treatment of the present invention are those combinations of texaphyrins (such as motexafin gadolinium), chemotherapeutic agents (such as doxorubicin) and/or co-therapeutic agents (such as ionizing, photodynamic and sonodynamic energy sources) previously disclosed, for example, in U.S. Pat. No. 5,776,925 and in WO00/01414. However, to the extent that pharmacologically active mediators of oxidative stress have not previously been disclosed for administration in combination with a texaphyrin, such as thiol-depleting agents (especially BSO), mitochondrial inhibitors (such as antimycins A) and certain redox cycling agents (e.g., excluding doxorubicin) are intended to be within the scope of the invention. Similarly excluded is the co-administration of ascorbic acid with cobalt or iron phthalocyanines and naphthalocyanines (e.g., as disclosed in U.S. Pat. No. 6,004,953), but, not when combined with the administration of ionizing radiation.

Utility

Methods for determining compounds which are useful as radiation sensitizers provide a facile means to assess the potential of such compound for use as adjuncts in treating tumors with ionizing radiation. In addition, the fact that such compounds produce one or more reactive oxygen species in vivo dictates that these compounds will be useful in their own right in killing cells such as tumor cells even in the absence of ionizing radiation.

When employed with ionizing radiation, the amount of compound administered to the patient will vary depending upon what is being administered, the purpose of the administration, the state of the patient, the manner of administration, and the like. In particular, a sufficient amount of the compound is administered to the cell or to the patient to therapeutically enhance the effect of ionizing radiation on tumor cell death. An amount adequate to accomplish this is defined as "therapeutically effective dose." Amounts effective for this use will depend on the judgment of the attending clinician depending upon factors such as the degree or severity of the cancer in the patient, the age, weight and general condition of the patient, and the like. Preferably, radiation sensitizing compounds used in conjunction with ionizing radiation are administered at dosages ranging from about 0.1 to about 100 mg/kg/day. Preferably, the active agent is administered approximately 2–5 hours prior to exposure to ionizing radiation.

When employed in the absence of ionizing radiation, the amount of compound administered to the patient will again vary depending upon what is being administered, the purpose of the administration, the state of the patient, the manner of administration, and the like. In particular, a sufficient amount of the compound is administered to the cell or to the patient so as to generate reactive oxygen species in quantities effective to initiate tumor cell death. An amount adequate to accomplish this is defined as "therapeutically effective dose." Amounts effective for this use will depend on the judgment of the attending clinician depending upon factors such as the degree or severity of the cancer in the patient, the age, weight and general condition of the patient, and the like. Preferably, when so employed, the compound is administered at dosages ranging from about 0.1 to about 100 mg/kg/day.

Similarly, drugs co-administered to the patient such as DNA alkylators, topoisomerase inhibitors, redox cycling agents, thiol-depleting agents and metabolic inhibitors are also employed in sufficient quantities for their intended purpose. These amounts are well documented in the art.

As noted above, the compounds administered to a patient are in the form of pharmaceutical compositions described herein. These compositions may be sterilized by conventional sterilization techniques, or may be sterile filtered. When aqueous solutions are employed, these may be packaged for use as is, or lyophilized, the lyophilized preparation being combined with a sterile aqueous carrier prior to administration. The pH of the compound preparations typically will be between 3 and 11, more preferably from 5–9 and most preferably from 7 and 8. It will be understood that use of certain of the foregoing excipients, carriers, or stabilizers will result in the formation of pharmaceutical salts.

Pharmaceutical Formulations

When employed as pharmaceuticals, compounds described herein are usually administered in the form of pharmaceutical compositions. These compounds can be administered by a variety of routes including oral, intravenous, intramuscular, and the like. These compounds are effective as both injectable and oral compositions. Such compositions are prepared in a manner well known in the pharmaceutical art and comprise at least one active compound.

These pharmaceutical compositions contain, as the active ingredient, one or more of the compounds described herein associated with pharmaceutically acceptable carriers. In making these compositions, the active ingredient is usually mixed with an excipient. When the excipient serves as a diluent, it can be a solid, semi-solid, or liquid material, which acts as a vehicle, carrier or medium for the active ingredient. Thus, the compositions can be in the form of tablets, pills, elixirs, suspensions, emulsions, solutions, syrups, and the like containing, for example, up to 10% by weight of the active compound, soft and hard gelatin capsules, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the active ingredient is employed at no more than about 20 weight percent of the pharmaceutical composition, more preferably no more than about 15 weight percent, with the balance being pharmaceutically inert carrier(s).

An active compound is typically effective over a wide dosage range and is generally administered in a pharmaceutically effective amount. It, will be understood, however, that the amount of the active ingredient actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

By way of example, the radiation sensitizer motexafin gadolinium is administered in a solution containing 2 mM optionally in 5% mannitol USP/water (sterile and non-pyrogenic solution). Dosages of 0.1 mg/kg up to as high as about 23.0 mg/kg have been delivered, preferably about 3.0 to about 15.0 mg/kg (for volume of about 90 to 450 mL) may be employed, optionally with pre-medication using anti-emetics above about 6.0 mg/kg. The texaphyrin is administered via intravenous injection over about a 5 to 10 minute period, followed by a waiting period of about 2 to 5 hours to facilitate intracellular uptake and clearance from the plasma and extracellular matrix prior to the administration of radiation.

When employing radiation therapy, a palliative course of 30 Gy in ten (10) fractions of radiation are typically administered over consecutive days excluding weekends and holidays. In the treatment of brain metastases, whole brain megavolt radiation therapy is delivered with 60Co teletherapy or a >4 MV linear accelerator with isocenter distances of at least 80 cm, using isocentric techniques, opposed lateral fields and exclusion of the eyes. A minimum dose rate at the midplane in the brain on the central axis is about 0.5 Gy/minute.

Radiation sensitizers may be administered before, or at the same time as, or after administration of the ionizing radiation, preferably before. The radiation sensitizer may be administered as a single dose, as an infusion, or it may be administered as two or more doses separated by an interval of time. Where the radiation sensitizer is administered as two or more doses, the time interval between administrations may be from about one minute to a number of days, preferably from about 5 min to about 1 day, more preferably about 4 to 5 hr. The dosing protocol may be repeated, from one to ten or more times, for example. Dose levels for radiation sensitization using motexafin gadolinium may range from about 0.05 $\mu$mol/kg to about 20 $\mu$mol/kg administered in single or multiple doses (e.g. before each fraction of radiation). A lower dosage range is presently preferred for intra-arterial injection or for impregnated stents. In the case of texaphyrins incorporating or conjugated to a radioisotope, the additional administration of radiation as a co-therapeutic agent is optional.

Administering a radiation sensitizer to a mammalian host bearing atheroma cells may be prior to, concurrent with, or following vascular intervention, and the interventon is followed by radiation. The administration may begin prior to, such as about 24–48 hours prior to, or at a time roughly accompanying vascular intervention, for example. Multiple or single treatments prior to, at the time of, or subsequent to the procedure may be used. "Roughly accompanying the vascular intervention" refers to a time period within the ambit of the effects of the vascular intervention. Typically, an initial dose of the sensitizer and radiation will be within 1–24 hours of the vascular intervention, preferably within about 5–24 hours thereafter. Follow-up dosages may be made at weekly, biweekly, or monthly intervals. Design of particular protocols depends on the individual subject, the condition of the subject, the design of dosage levels, and the judgment of the attending practitioner. In the methods of the invention involving the administration of a compound that catalyzes the production of one or more reactive oxygen species from a cellular metabolite having a standard biochemical reduction potential more negative than the standard biochemical reduction of oxygen/hydrogen peroxide, a source or precursor of such cellular metabolite is co-administered either before, contemporaneously with the catalytic agent or subsequent to its administration; either or both agents may be administered systemically or locally (e.g., by intra-arterial injection).

The following formulation examples illustrate representative pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50 to 60 C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 4

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 5

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 6

Capsules are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 7

An injectable preparation buffered to a pH of 7.4 is prepared having the following composition:

| Ingredients | Amount |
|---|---|
| Active Ingredient | 0.2 g |
| Sodium Phosphate Buffer Solution (0.8M) | 10.0 ml |
| DMSO | 1.0 ml |
| WFI | q.s. to 100 ml |

Formulation Example 8

An injectable formulation is prepared having the following composition:

| Ingredients | Amount (w/v %) |
|---|---|
| Motexafin gadolinium | 0.23% |
| Motexafin lutetium | 0.20% |
| Mannitol (USP) | 5.0% |
| Acetic Acid (5%) | adjust to pH 5.4 |
| Sterile WFI (USP) | q.s. to 100% |

The formulation is filled into a glass vials, which are then purged with nitrogen to exclude oxygen from the head space and then sealed.

It may be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Patent 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa. 17th ed. (1985).

The following examples are offered to illustrate this invention and are not to be construed in any way as limiting the scope of this invention.

EXAMPLES

In the examples below, the following abbreviations have the following meanings. If an abbreviation is not defined, it has its generally accepted meaning.

| | |
|---|---|
| BSO = | buthionine sulfoximine |
| CdTex = | compound of formula II where M is $Cd^{2+}$ |
| CoTex = | compound of formula II where M is $Co^{3+}$ |
| Di-amino GdTex = | compound of formula II where M is $Gd^{3+}$ except that both $R^1$ (as shown in formula I) is aminopropyl |
| Di-amino LuTex = | compound of formula II where M is $Lu^{3+}$ except that both $R^1$ (as shown in formula I) is aminopropyl |
| DyTex = | compound of formula II where M is $Dy^{3+}$ |
| EuTex = | compound of formula II where M is $Eu^{3+}$ |
| $Fe(Tex)_2O$ = | mu-oxo dimer of two compounds of formula II where M is $Fe^{2+}$ |
| GdTex = | motexafin godolinium (formula II where M is $Gd^{3+}$) |
| HEPES = | hydroxyethylpiperizine ethane sulfonic acid |
| HPLC = | high performance liquid chromatography |
| LuTex = | motaxafin lutetium (formula II where M is $Lu^{3+}$) |
| mg = | milligram |
| mL = | milliliter |
| mm = | millimeter |
| mM = | millimolar |
| MnTex = | compound of formula II where M is $Mn^{2+}$ |
| mmol = | millimols |
| nm = | nanometer |
| psi = | pounds per square inch |
| RPMI 1640 = | a commercially available culture medium |
| SmTex = | compound of formula II where M is $Sm^{3+}$ |
| YTex = | compound of formula II where M is $Y^{3+}$ |
| μL = | microliter |
| μM = | micromolar |

Example 1

Oxidation of NADPH Under Approximate Physiologic Conditions

This example measures radiation sensitization potential as a function of oxidation of the cellular metabolite NADPH.

1A. Materials and Method
  The following stock solutions were prepared:
    Stock NADPH (Sigma N 7505) (prepared fresh daily): 12.2 mg/(10 mL. 833.4 mg/mmol)=1.46 mM
    Stock GdTex: 5.76 mg/(10.0 mL water. 1148 mg/mmol)= 501.7 µM
    Stock 4× Buffer: 200 mM HEPES, pH 7.5; 400 mM NaCl; 0.4 mM EDTA
    Stock LuTex: 5.02 mg/(10.0 mL water×1166 mg/mmol)= 431 µM
  These were combined to form the reaction mixtures analyzed by HPLC, for example:
    250 µL 4× Buffer, 250 µL NADPH Stock, 427 µL Water, 72.7 µL GdTex Stock
    250 µL 4× Buffer, 250 µL NADPH Stock, 457.7 µL Water, 42.3 µL LuTex Stock
  The HPLC Method employed was as follows:
1. HPLC Operating Parameters
  System—HPLC system capable of delivering gradient mobile phase
  Detector wavelength—260 nm
  Injection Volume—20 µL
  Pressure—ca.2000 psi
  Column Temperature—40° C.
  Column—Nucleogel DEAE 60-7 125×4 mm
2. Mobile Phase
  Solution A—0.75 M $KH_2PO_4$, pH 3.8
  Solution B—0.016 M $KH_2PO_4$, pH 3.8

| Time (min.) | Flow (mL/min) | A (%) | B (%) |
|---|---|---|---|
| inital | 1.0 | 5 | 95 |
| 5 | 1.0 | 5 | 95 |
| 30 | 1.0 | 80 | 20 |
| 31 | 1.5 | 5 | 95 |
| 39 | 1.0 | 5 | 95 |
| 40 | 1.0 | 5 | 95 |

A reaction mixture was prepared containing NADPH, water and sufficient buffer to maintain the solution at pH 7.5. Texaphyrin, 0.1 molar equivalent to the NADPH, was added to this reaction mixture, vortexed briefly, and then the solution placed in the HPLC sampler for immediate injection. Further injections were made at appropriate time points, whereupon the integrated peak areas of both NADPH and $NADP^+$ were measured and used to calculate the extent of reaction at a given time point.

Provided that the amount of texaphyrin was sufficiently low relative to substrate, the percentage of $NADP^+$ generated by the reaction plotted against time initially gave a straight line. (For LuTex, it was necessary to drop the catalyst concentration to ca. 0.05 equivalent.) The slope of initial time points (eg., plotting as mM concentration vs time in hours) provided a rate which was used as a point in a saturation (Michaelis-Menton) plot. This process was repeated at various concentrations of NADPH. Data (in triplicate) was fitted to the Michaelis-Menton equation (initial reaction velocity/catalyst concentration)=($k_{cat}$× substrate concentration)/($K_M$+substrate concentration), where substrate is NADPH, catalyst is texaphyrin complex, $k_{cat}$ is the first-order rate constant for the catalyst, and $K_M$ is the dissociation (or Michaelis) constant for the catalyst/substrate complex. For GdTex, $k_{cat}$=0.049 ±0.003 $min^{-1}$ and $K_M$=1.69±0.17 mM. For LuTex, $k_{cat}$=0.119±0.011 $min^{-1}$ and $K_M$=0.56±0.20 mM.

Figure 2:
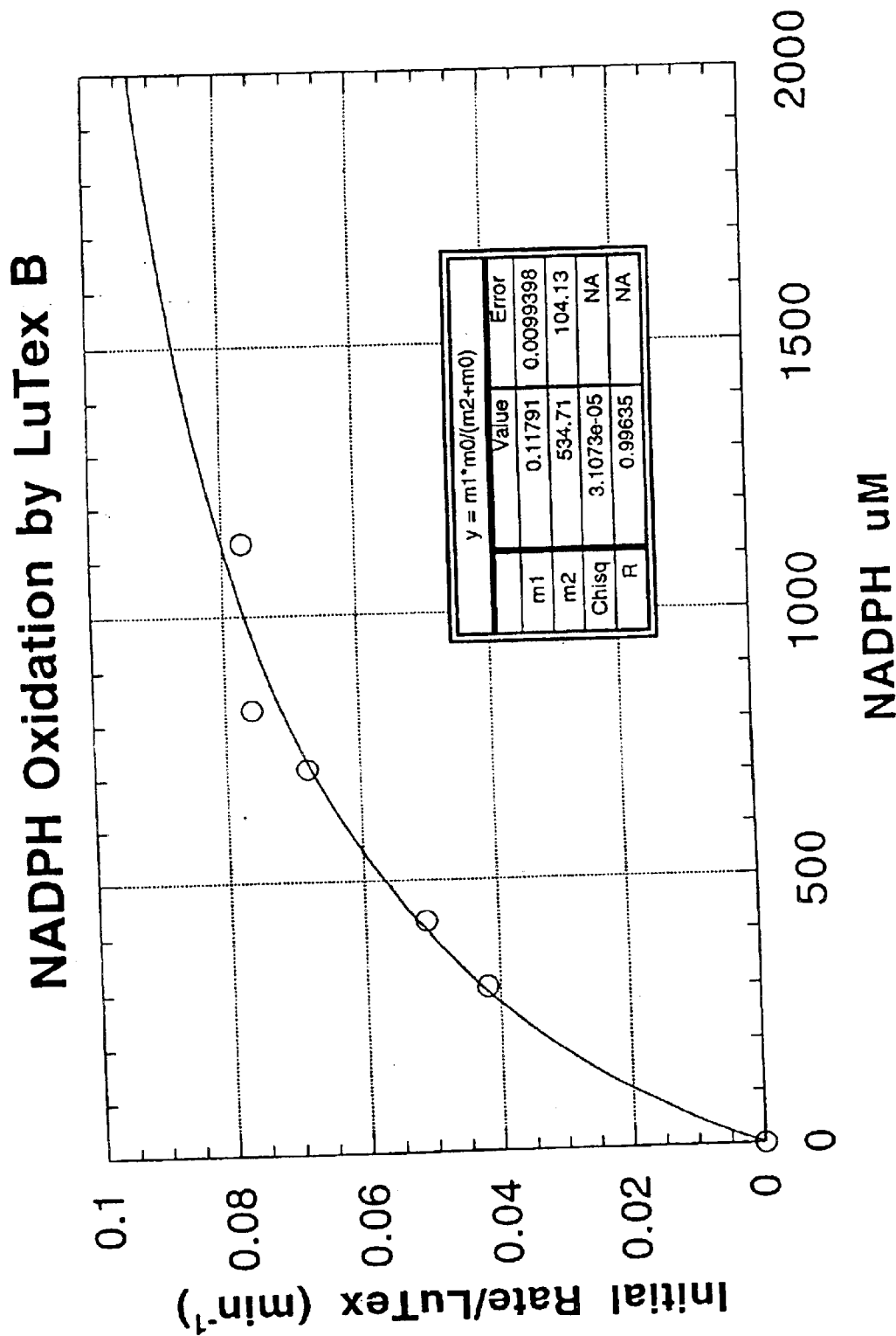
Figure 3:
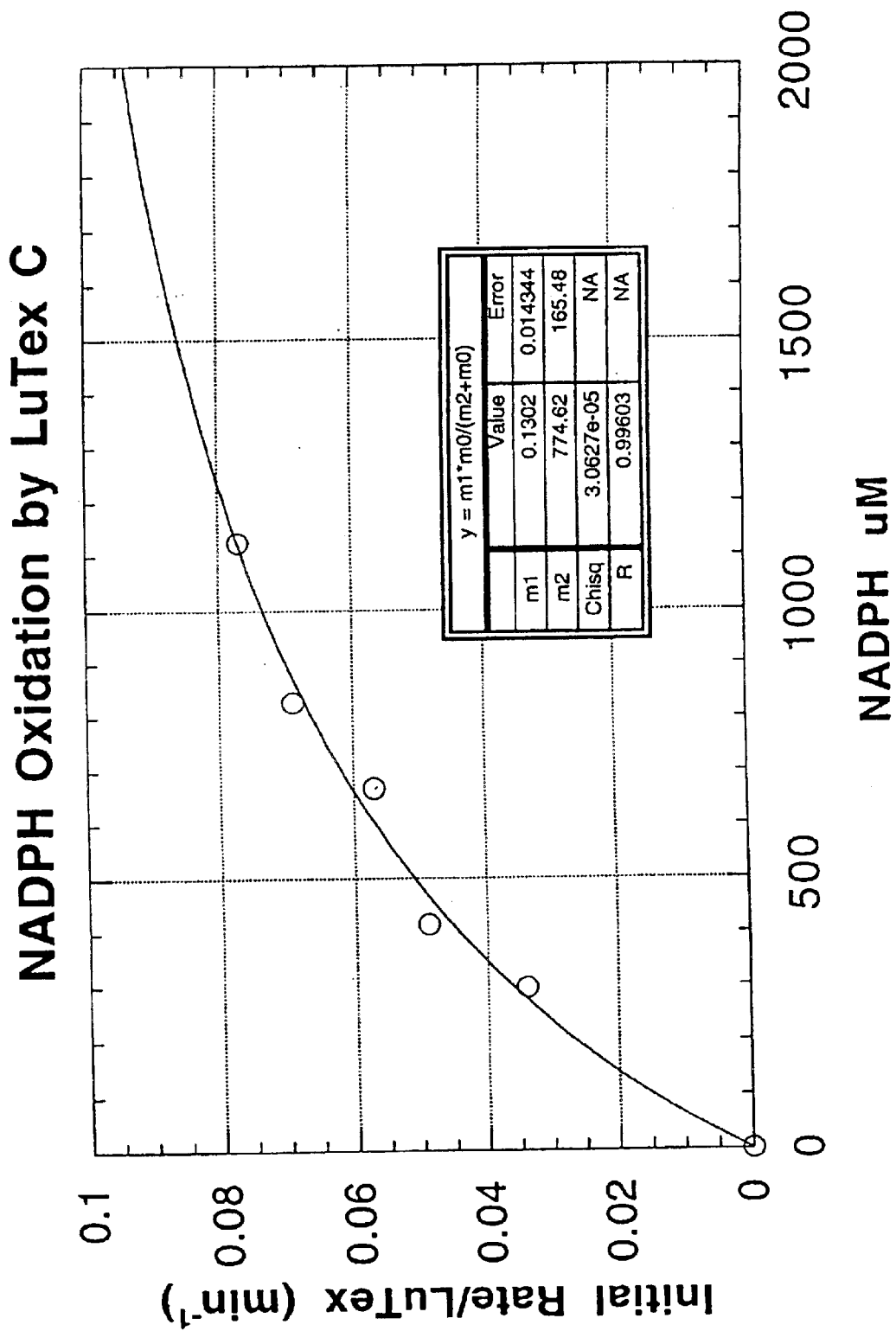
Figure 4:
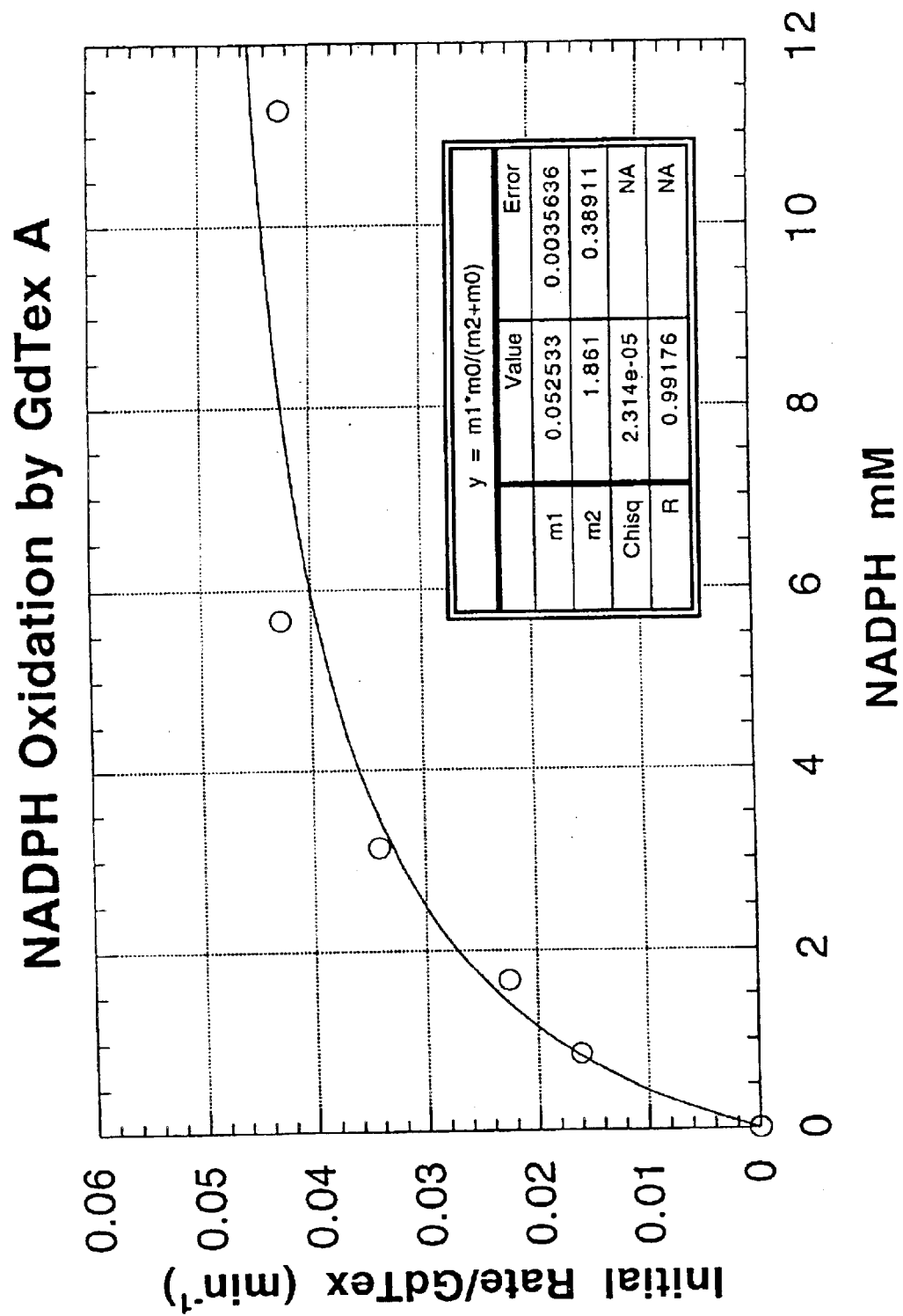
Figure 5:
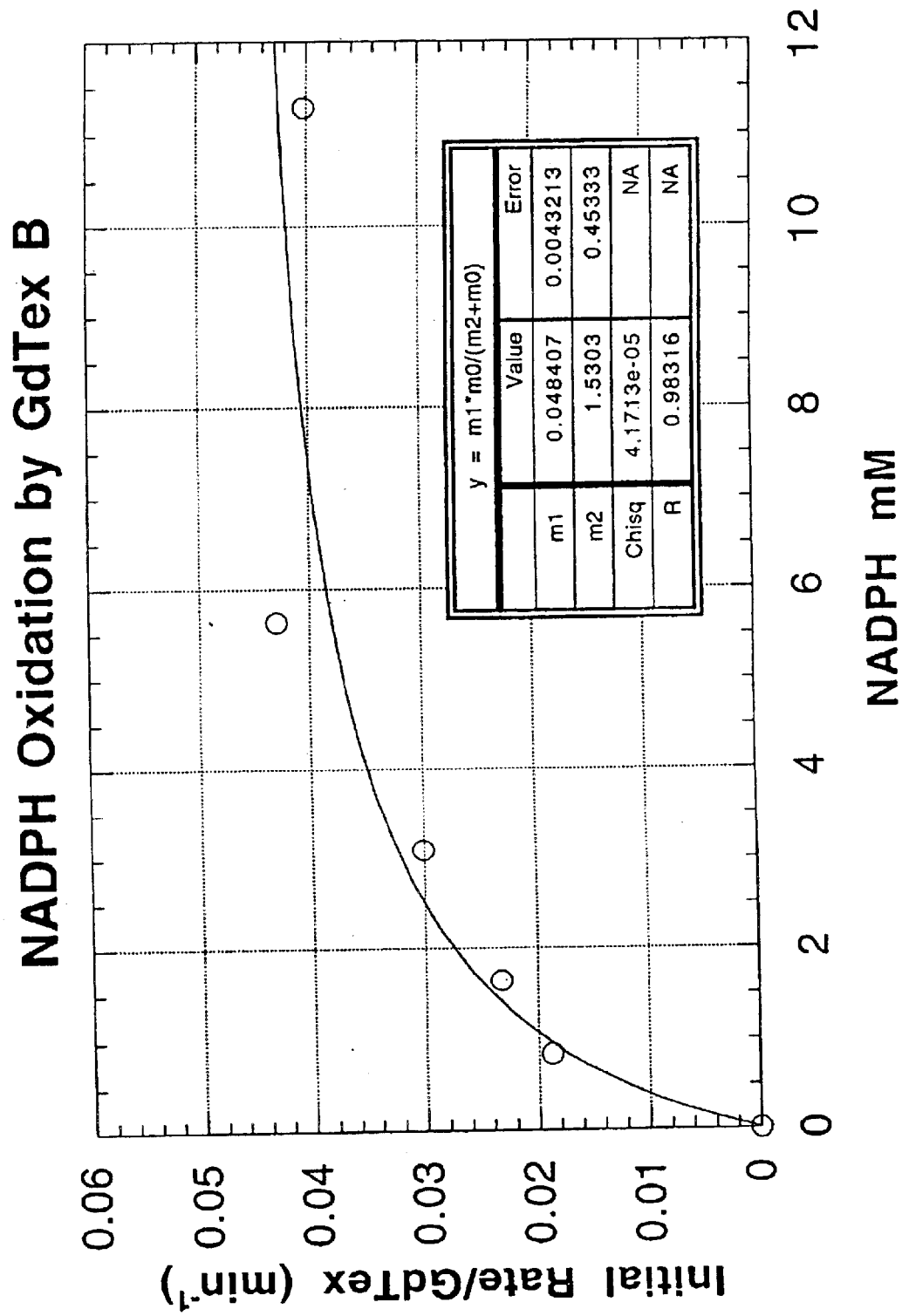
Figure 6:
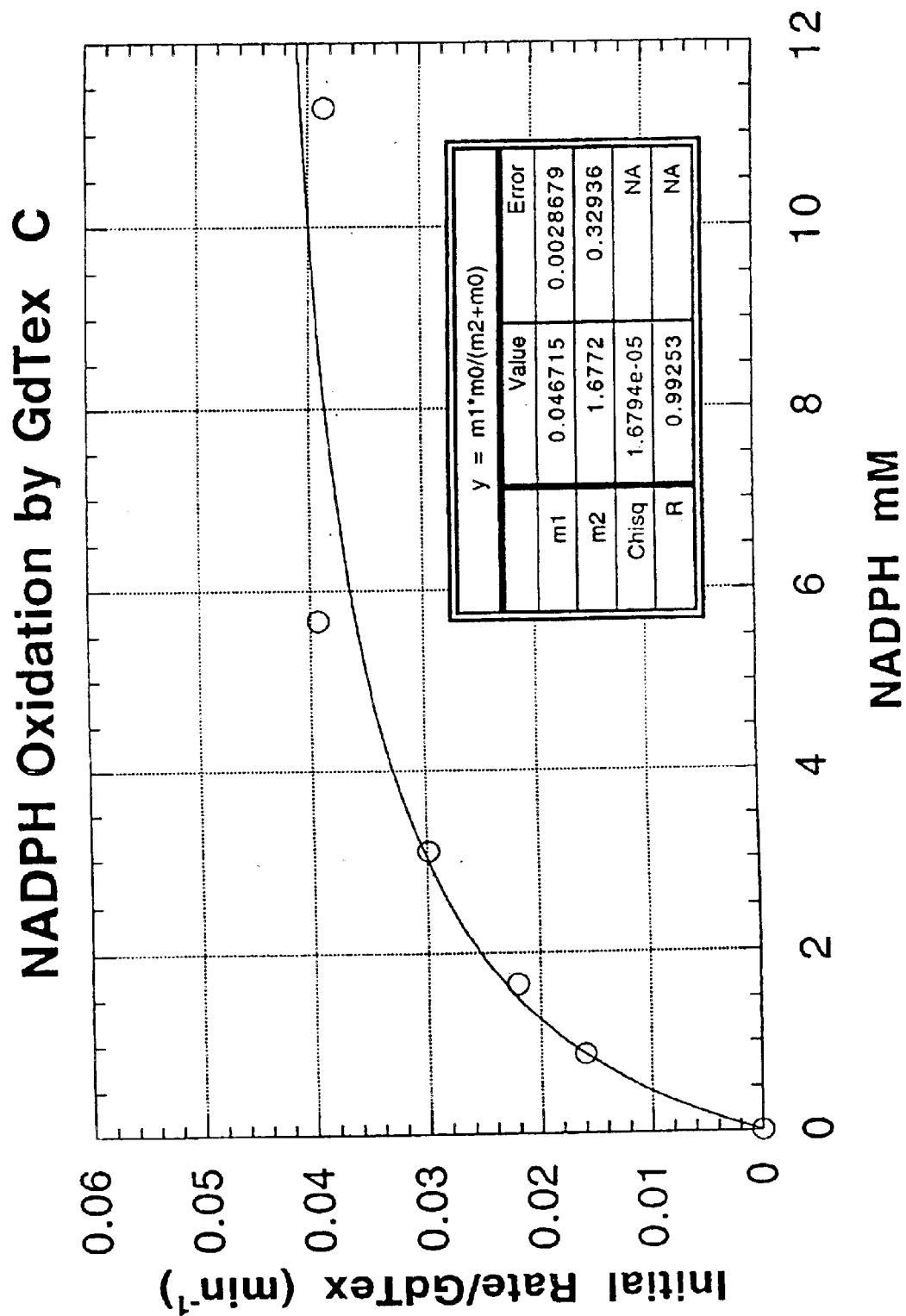

Results
The results of this analysis are depicted in FIGS. 1-6. FIGS. 1-3 illustrate triplicate runs for LuTex which runs are recited as LuTex A, LuTex B and LuTex C. FIGS. 4-6 illustrate triplicate runs for GdTex which runs are recited as GdTex A, GdTex B and GdTex C These results evidence that in the presence of texaphyrins, NADPH was oxidized to $NADP^+$, and further that the test compounds have probable radiation sensitization activity.

Figure 16:
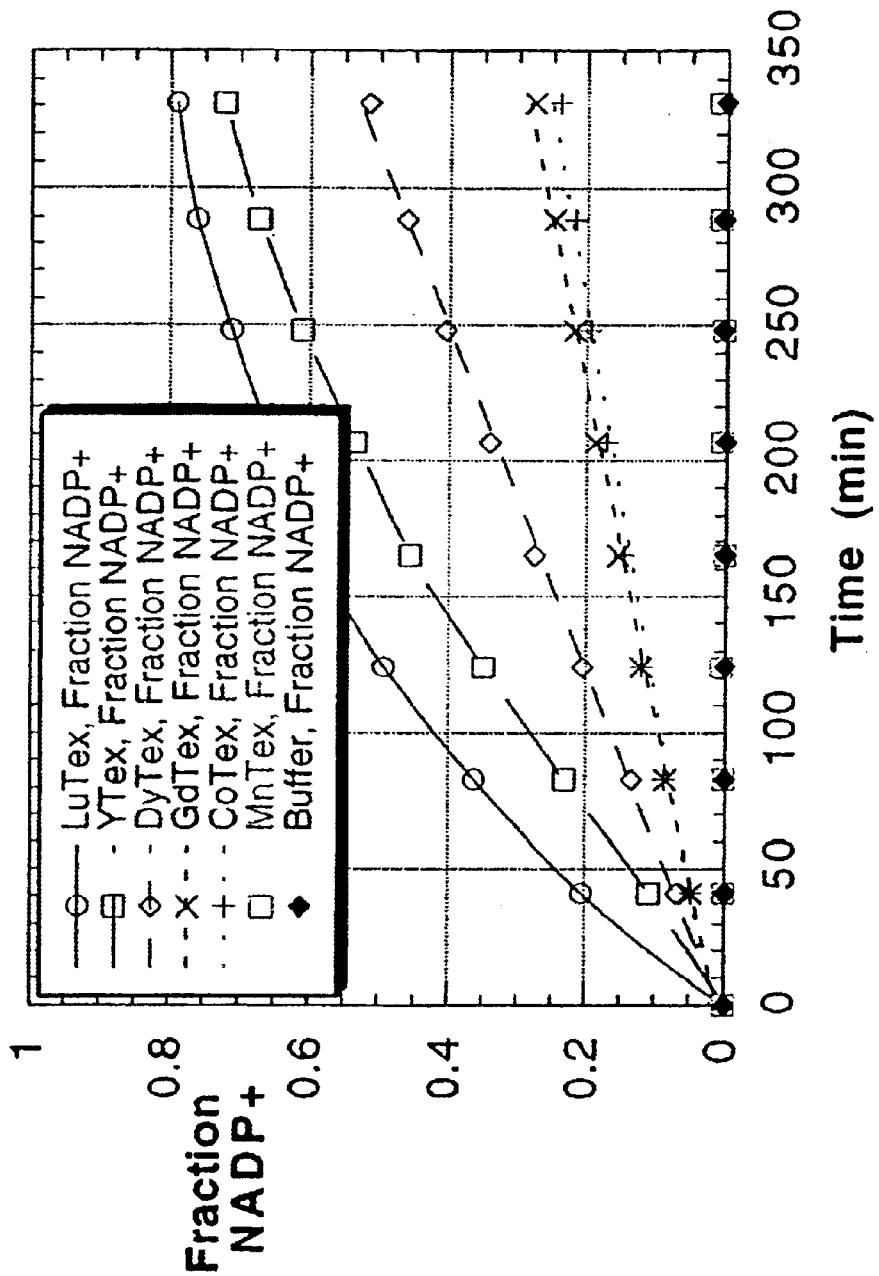
FIG. 16 illustrates the rate of NADPH oxidation versus time by various metal cation complexes of a texaphyrin.

1B. By following the procedure of Example 1A using a single concentration of NADPH and employing 0.1 equivalent of test compound, the results illustrated in FIG. 16 were obtained. These results evidence that in the presence of the tested texaphyrins, NAPDH was oxidized to $NADP^{30}$, and further that the test compounds (with the exception of $Mn^{2+}$Tex) have probable radiation sensitization activity where NADPH is the reducing metabolite.

Example 2
Oxidation of Ascorbate under Approximate Physiologic Conditions

This example measures radiation sensitization potential as a function the oxidation of ascorbate, employing an assay modified from Buettner, et al., Radiation Research 145:532–541 (1996).

2A. Materials and Method
  The following stock solutions were prepared:
    Stock ascorbic acid (Sigma A5960) (prepared fresh): 8.82 mg/(25 mL 176.1 mg/mmol)=2.00 mM
    Stock GdTex: 5.72 mg/(10.0 mL water. 1148 mg/mmol)= 498 µM
    Stock 4× Buffer: 200 mM HEPES, pH 7.5; 400 mM NaCl
  The stock solutions were prepared using ACS grade water (Aldrich 32,007-2). 4×buffer was prepared using NaCl 99.999% (Aldrich 20,443-9), HEPES (Gibco-BRL 11344-025), and sodium hydroxide 99.99% (Aldrich 30,657-6), and was treated with Chelex® 100 (BioRad 143-2832) prior to use to remove trace iron contaminants. These were combined to form the reaction mixture analyzed by UV-vis spectroscopy: 400 µL 4× Buffer, 200 µL Ascorbic Acid Stock, 979.9 µL Water, 20.1 µL GdTex Stock.

In brief, a reaction mixture was prepared containing ascorbate, buffer, and water. A lesser amount of texaphyrin catalyst, eg., 0.025 molar equivalent, was added to this reaction mixture, vortexed briefly, and placed in a quartz cuvette (0.2, 0.5, 1.0, 2.0, 5.0, or 10 mm path length as needed to give ca. 1.8 absorbance reading at 266 nm). The cuvette was placed in a UV-vis spectrophotometer and the absorbance was read every 60 seconds for ten minutes. The absorbance at 266 nm plotted against time initially gaive a straight line. The slope of initial time points (eg., plotting as M concentration vs time in minutes) provided a rate which was used as a point in a saturation (Michaelis-Menton) plot. This process was repeated at various concentrations of ascorbate. A background rate of ascorbate oxidation was also measured at each concentration of ascorbate using this procedure without GdTex catalyst. The resulting background rate of oxidation was subtracted from the rate of oxidation in the presence of catalyst. Data was fitted to the Michaelis-Menton equation (initial reaction velocity/ catalyst concentration=($k_{cat}$×substrate concentration)($K_M$+ substrate concentration), where substrate was ascorbate, catalyst was texaphyrin complex, $k_{cat}$ is the first-order rate constant for the catalyst, and $K_M$ is the dissociation (or Michaelis) constant for the catalyst/substrate complex. For GdTex, $k_{cat}$=0.35 min-1 and $K_M$=1.06 mM.

Results

Figure 7:
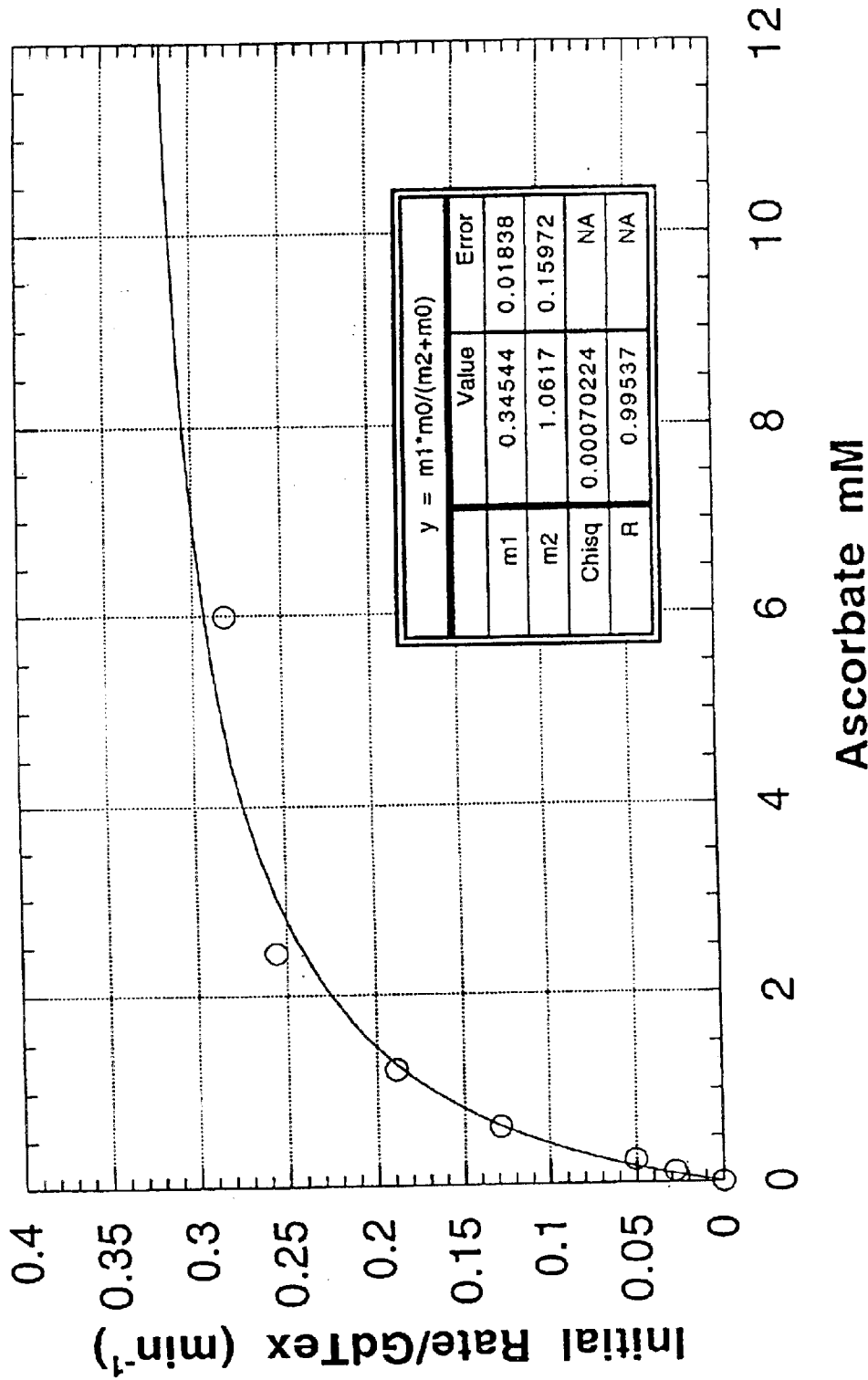
FIG. 7 illustrates the rate of ascorbate oxidation versus ascorbate concentration in the presence of GdTex.

The results of this analysis are depicted in FIG. 7 which results demonstrate that in the presence of GdTex, ascorbate was oxidized and further that the test compounds have probable radiation sensitization activity.

2B

By following the procedure of Example 2A and substituting motexafin gadolinium with motexafin lutetium it was determined that ascorbate was oxidized in the presence of motexafin lutetium but to a lesser extent than in the presence of motexafin gadolinium. Thus, taken in conjunction with the results of Example 1, probable radiation sensitization activity of motexafin lutetium is associated with a NADPH metabolic pathway, whereas the probable radiation sensitization activity of motexafin gadolinium is more strongly associated with an ascorbate metabolic pathway, suggesting that co-administration of both motexafin gadolinium and motexafin lutetium can combine to more effectively catalyze the production of hydrogen peroxide from both pathways.

2C

By following the procedure of Example 2A and substituting iron porphyrin for the texaphyrin, it is indicated that ascorbate can be similarly oxidized and that the test compound will have probable radiation sensitization activity.

2D

By following the procedure of Example 2A, using an initial ascorbate concentration of 1.23 mM and a texaphyrin concentration of 61.5 $\mu$M, the results summarized in below in Table 1 were obtained.

TABLE 1

| Texaphyrin | Ascorbate Depletion initial rate ($V_O$) $\mu$M/min |
|---|---|
| LuTex | −2.33 ! 0.16 |
| ErTex | −3.55 |
| DyTex | −5.92 |
| GdTex | −9.98 ! 1.03 |
| EuTex | −9.45 ! 0.91 |
| SmTex | −10.45 ! 0.50 |
| NdTex | −8.85 ! 0.20 |
| MnTex | −3.0 |
| (FeTex)$_2$O | −30.6 |
| CoTex | −28.9 |
| CdTex | −3.4 |
| Di-amino MnTex | −3.4 |
| Di-amino GdTex | −10.3 |
| Di-amino LuTex | −9.7 |

These results eivdence that in the presence of the tested texaphyrins, ascorbate was oxidized, and further that the test compounds have probable radiation sensitization activity.

Example 3
Production of $H_2O_2$ in the Presence of NADPH under Approximate Physiologic Conditions This example illustrates the measurement of hydrogen peroxide generation from the oxidation of NADPH, as an indicator of radiation sensitization potential.

3A. Materials and Method

The following stock solutions were prepared:
Stock NADPH (Sigma N 7505) (prepared fresh): 10.14 mg/(10 mL×833.4 mg/mmol)=1.217 mM
Stock LuTex: 5.02 mg/(10.0 mL water×1166 mg/mmol)= 431 M
Stock 4× Buffer: 200 mM HEPES, pH 7.5; 400 mM NaCl
These were combined to form the reaction mixture: 200 $\mu$L 4× Buffer, 200 $\mu$L NADPH Stock, 371.8 $\mu$L Water, 28.2 $\mu$L LuTex Stock. This was analyzed as indicated below. As a control, a solution in which the LuTex complex was not added was prepared as above, with suitable adjustment of the volume of water, and analyzed concurrently. In similar manner, a solution was prepared as above except that 2 $\mu$L catalase (Boeringer-Mannheim 106 836, now Roche Molecular Biochemicals, Indianapolis, Ind.) was added, and analyzed concurrently.

A reaction mixture was prepared containing NADPH, buffer, and water. Texaphyrin catalyst, eg., 0.05 molar equivalent, was added to this reaction mixture, vortexed briefly, and incubated at ambient temperature in the dark. Aliquots of 50 L were removed every 20 minutes, and added to a reagent which produces a characteristic color in the presence of $H_2O_2$ (Bioxytech® $H_2O_2$-560™, R&D Systems, Minneapolis, Minn.). A 25 mM solution of $H_2O_2$ was prepared by dilution of 30% $H_2O_2$. The absorbance at 240 nm was used to standardize this solution, which was further diluted and used to construct a standard $H_2O_2$ curve at 560 nm in conjunction with the $H_2O_2$ colorimetrc reagent. Further details on the use of the Bioxytech® $H_2O_2$-560™ kit are available from the package insert.

Measurements of the absorbance at 560 nm (with appropriate subtraction of the background absorbance of the reagent at this wavelength) were made of samples taken at the various time points.

Results

Figure 8:
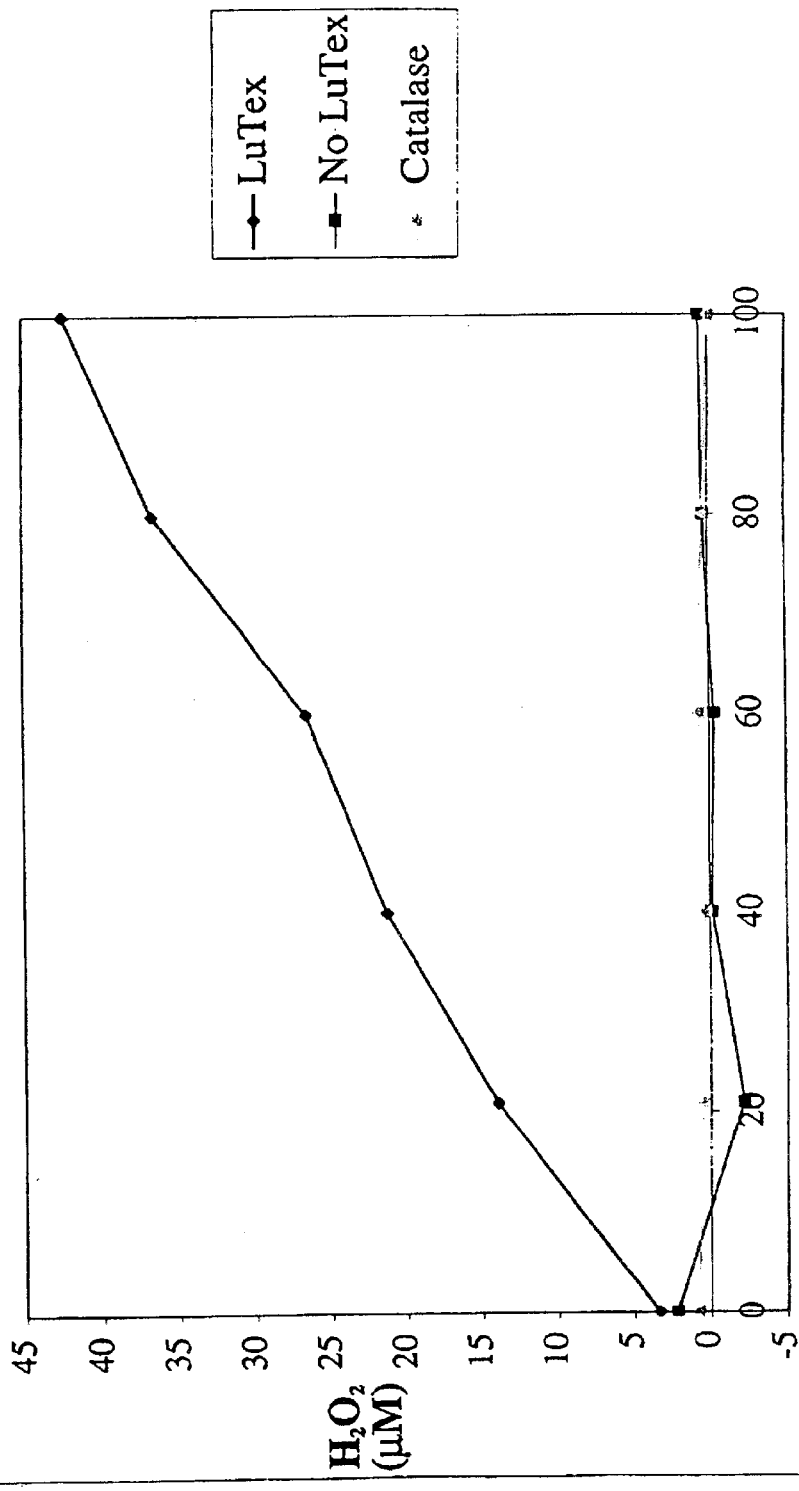
FIG. 8 illustrates the quantity of hydrogen peroxide generated by the addition of LuTex to NADPH as compared to control or to a LuTex/NADPH solution further containing catalase.

After conversion of absorbance to $H_2O_2$, a plot of $H_2O_2$ vs. time showed that $H_2O_2$ was produced only in the reaction mixture which contained LuTex and no catalase. Approximately 40 $\mu$M $H_2O_2$ was produced over the course of 100 minutes. The results of this example are illustrated in FIG. 8, which demonstrates that in the presence of LuTex, NADPH generates hydrogen peroxide. The test compound has probable radiation sensitization activity.

3B

By following the procedure of Example 3A and substituting redox cycling agents for the texaphyrin, it is indicated that reactive oxygen species can be similarly generated and that the test compound will have probable radiation sensitization activity. Suitable redox cycling agents for use in this example include, for instance, alloxan, phenazine methosulfate, menadione, copper/putrescine/pyridine, methylene blue, paraquat, doxorubicin and ruthenium (II) tris-(1,10-phenanthroline-5,6-dione). To the extent these redox cycling agents do not preferentially accumulate in tumors, such molecules can be coupled to a compound that does preferentially accumulate in a tumor.

Example 4
Production of $H_2O_2$ in the Presence of Ascorbate under Approximate Physiologic Conditions This example illustrates the measurement of hydrogen peroxide generation from the oxidation of ascorbate, as an indicator of radiation sensitization potential.

In this example, the following stock solutions were prepared:
Stock ascorbic acid (Sigma A 5960) (prepared fresh): 9.98 mg/(10 mL×176.12 mg/mmol)=5.67 mM
Stock GdTex: 5.76 mg/(10.0 mL water×1148 mg/mmol)= 502 $\mu$M
Stock 4× Buffer: 200 mM HEPES, pH 7.5; 400 mM NaCl
These were combined to form the reaction mixture: 200 $\mu$L 4× Buffer, 39 $\mu$L ascorbic acid Stock, 517.3 $\mu$L Water, 43.7 $\mu$L GdTex Stock. The reaction mixture was analyzed for hydrogen peroxide as indicated above. As a control, a solution in which complex was not added was prepared as above, with suitable adjustment of the volume of water, and analyzed concurrently.

Measurements of the absorbance at 560 nm (with appropriate subtraction of the background absorbance of the reagent at this wavelength) were made of samples taken at the various timepoints. It was noted that the control solution gave a uniform background absorbance which was similar at all time points, whereas the mixture containing GdTex gave an increasing amount of absorbance over time. (Sugars are known to produce high background absorbance in this assay, see manufacturers insert for details.)

Results

Figure 9:
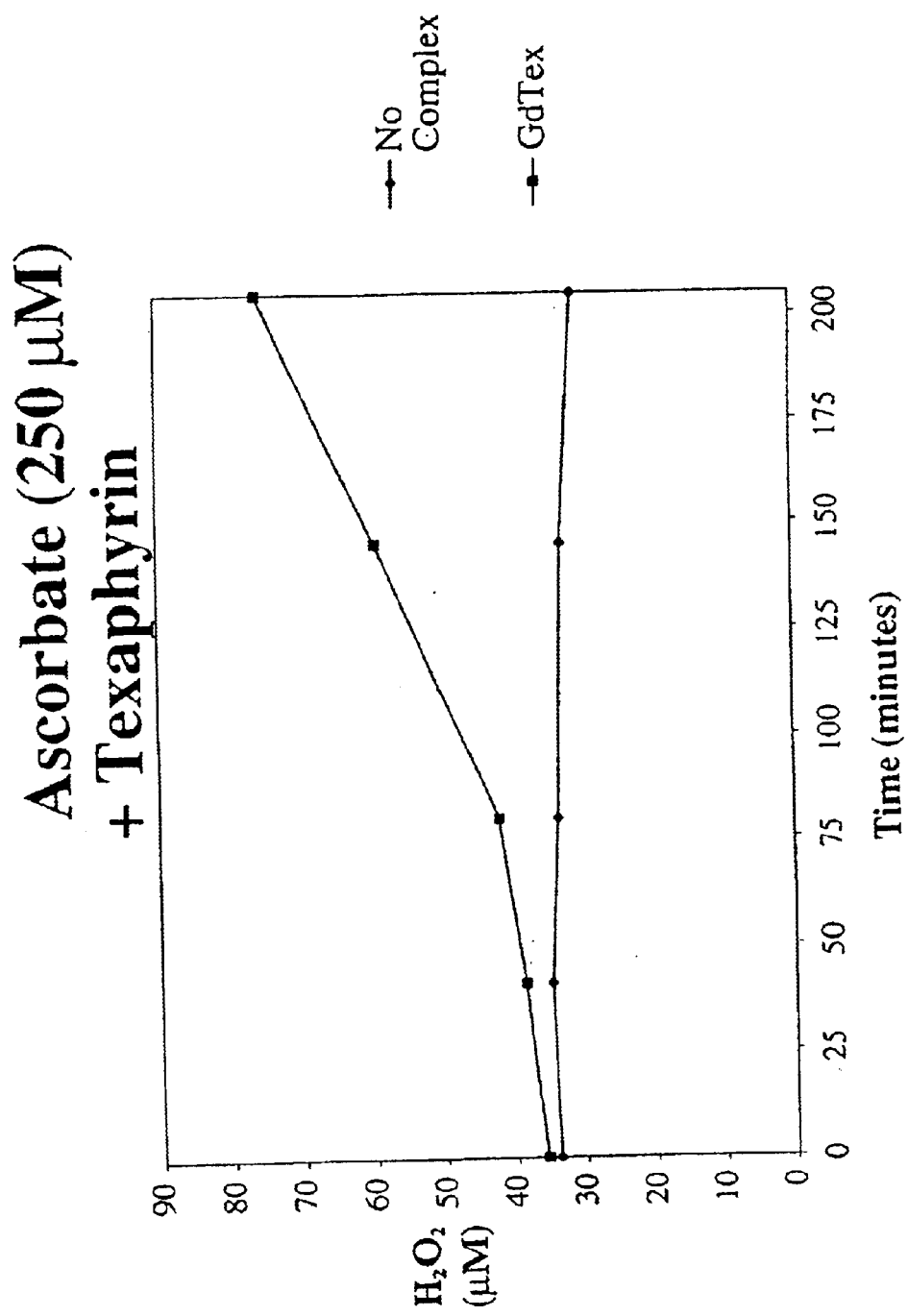
FIG. 9 illustrates the quantity of hydrogen peroxide generated by the addition of GdTex to ascorbate as compared to control.

After conversion of absorbance to $H_2O_2$, a plot of $H_2O_2$ vs. time showed that $H_2O_2$ was produced in the reaction mixture which contained GdTex. The plot (FIG. 9) was linear over the time interval of 75 to 200 minutes, with approximately 35 $\mu$M $H_2O_2$ produced over this interval. This demonstrates that in the presence of GdTex, ascorbate generates hydrogen peroxide. The test compound has probable radiation sensitization activity.

Example 5

Production of $H_2O_2$ by the Gadollnium(III) Complex of Texaphyrin in the Presence of Ascorbate under Cell Culture Conditions The proliferation of MES-SA human uterine cells (Harker, W. G.; MacKintosh, F. R.; Sikic, B. I. *Cancer Res.* 1983, 43, 4943–4950) grown in RPMI-1640 medium in the presence of ascorbate or complex was used to assess the formation of hydrogen peroxide under cell culture conditions.

5A. Materials and Methods

MES-SA cells were allowed to adhere to (4) 96-well microtiter plates (4000 cells per well) overnight in 160 $\mu$L RPMI medium. Stock ascorbate 3.0 mM in medium (80 $\mu$L) was serially diluted (1:3) in rows B through F (discarding the final 80 $\mu$L). Row G was used for no-ascorbate control. Stock solutions of GdTex (2 mM in 5% mannitol) diluted in medium and 5% mannitol were prepared and added to the plates to give a final volume of 200 $\mu$L in all wells. Columns 2 and 3 contained 100 $\mu$M GdTex; columns 4 and 5 contained 75 $\mu$M GdTex, columns 6 and 7 contained 50 $\mu$M GdTex; columns 8 and 9 contained 25 $\mu$M GdTex; and columns 10 and 11 contained no GdTex (all concentrations final). Final mannitol concentration was 0.25% in all wells. The plates were incubated at 37 C. under a 5% CO2/95% air atmosphere. Complex-containing medium was exchanged for fresh medium after 5 hours, and plates were incubated an additional 72 hours prior to analysis for viability using the tetrazolium dye, MTT (Mosmann, T. *J. Immunol. Methods* 1983, 65, 55–63). In brief, 20 $\mu$L MTT dye (Sigma Chemical, St. Louis, Mo., catalogue no. M 2128, 5 mg/mL solution in phosphate buffered saline) was added to cells in media to give a final volume of 200 $\mu$L. The plates were incubated at 37° C. for ca. 2 hours, whereupon the media was removed and isopropyl alcohol (100 $\mu$L/well) was added. Plates were vortexed for ca. 3 minutes to dissolve MTYT formazan, then read on a microplate reader at 560-650 nm. Plate absorbances were normalized to wells containing neither ascorbate nor GdTex to allow plate to plate comparison. Data for each concentration of GdTex and ascorbate is the average of eight wells.

Results

Ascorbate alone had no inhibitory effect at concentrations at or below 333 $\mu$M in the absence of GdTex, whereas complete cytotoxicity was observed at all concentrations of GdTex at this concentration of ascorbate. GdTex had no cytotoxic effect in the absence of ascorbate. A dose-response was observed towards GdTex at 111 $\mu$M and 62.5 $\mu$M concentrations of ascorbate.

Figure 10:
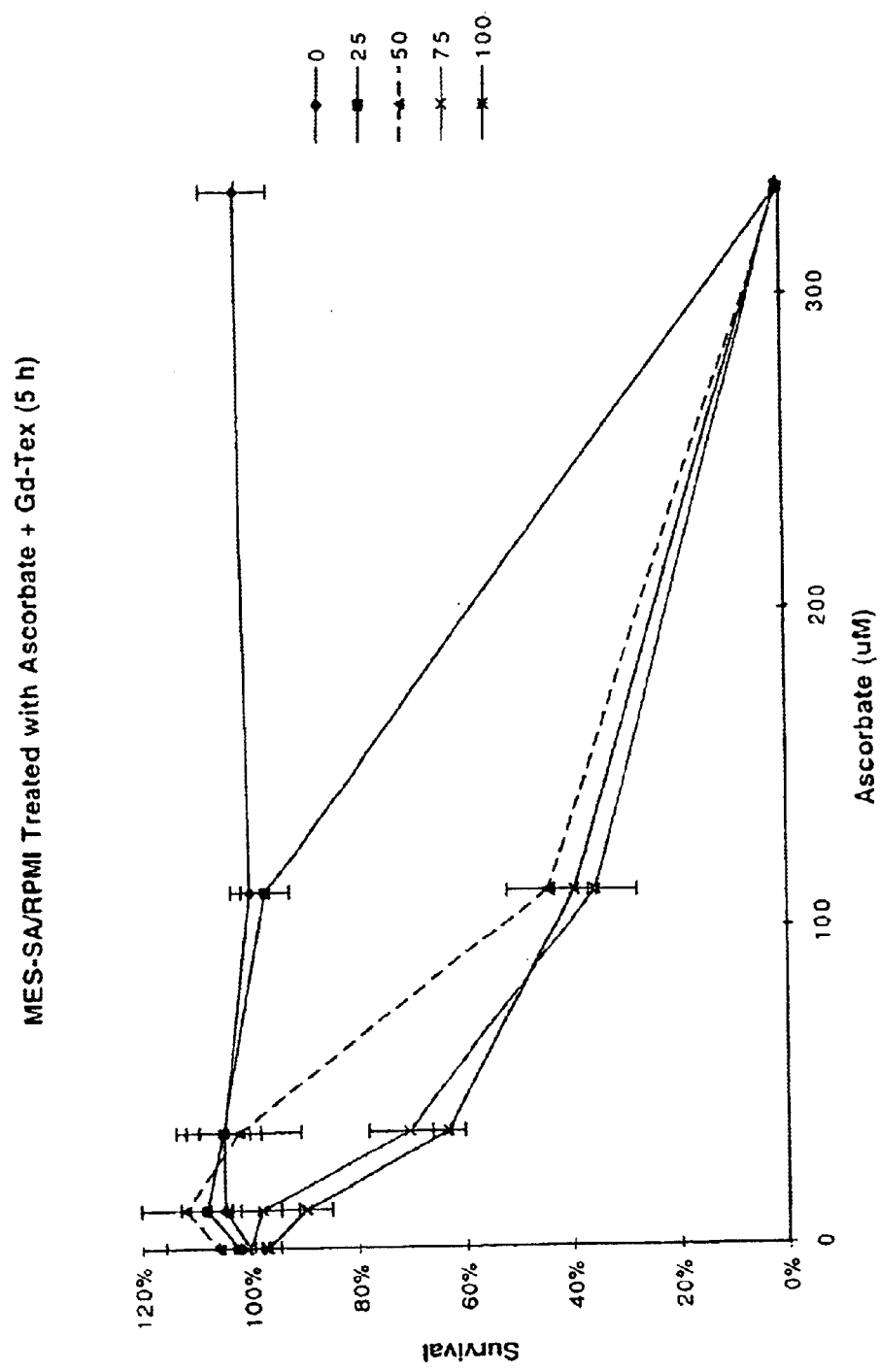
FIG. 10 illustrates the percent survival of MES-SA human uterine cells in the presence of varying concentrations of ascorbate and varying concentrations of GdTex.

The results of this analysis are illustrated in FIG. 10. The toxicity of cells to the combination of sufficient concentrations of GdTex and ascorbate is attributed to the production of toxic quantities of hydrogen peroxide and suggests that motexafin gadolinium has probable radiation sensitization activity.

Example 6

Production of $H_2O_2$ by the Lutetium(III) Complex of Texaphyrin in the Presence of Ascorbate under Cell Culture Conditions The proliferation of MES-SA human uterine cells grown in RPMI-1640 medium in the presence of ascorbate and LuTex was used to assess the production of hydrogen peroxide under cell culture conditions following the protocol outlined in the previous example. Ascorbate alone had no inhibitory effect at concentrations at or below 333 $\mu$M in the absence of LuTex, whereas a dose-response was observed towards LuTex at this concentration. No inhibitory effect was seen at lower concentrations of ascorbate. LuTex had no inhibitory effect in the absence of ascorbate.

Figure 11:
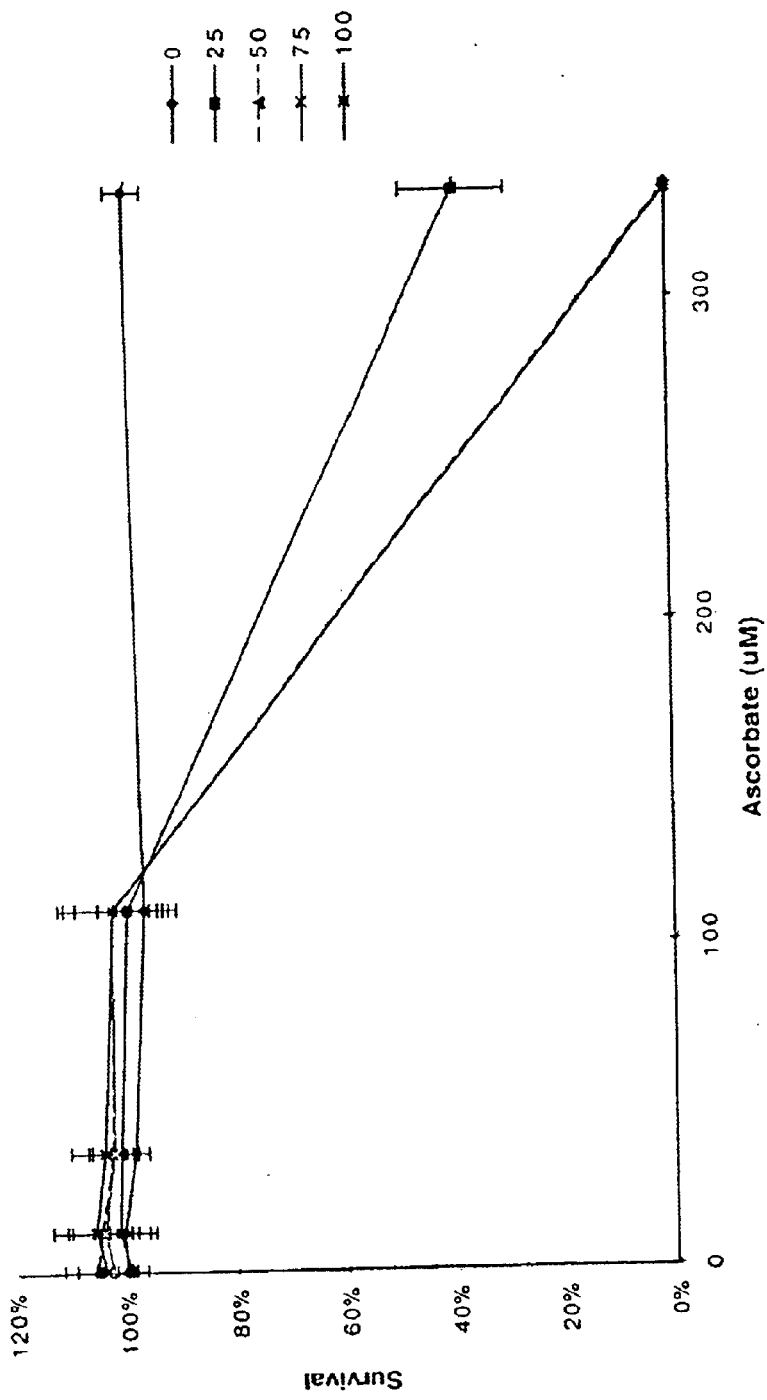
FIG. 11 illustrates the percent survival of MES-SA human uterine cells in the presence of varying concentrations of ascorbate and varying concentrations of LuTex.

The results of this analysis are illustrated in FIG. 11. The toxicity of cells to the combination of sufficient concentrations of LuTex and ascorbate is attributed to the production of toxic quantities of hydrogen peroxide and suggests that LuTex has probable radiation sensitization activity.

Example 7

Production of $H_2O_2$ by the Lutetium(III) Complex of Texaphyrin in the Presence of NADPH under Cell Culture Conditions The proliferation of EMT-6 mouse mammary sarcoma (Rockwell, S. C., et al., *J. Natl. Cancer Inst.* 1972, 49, 735–749) cells grown in RPMI-1640 medium in the presence of NADPH and motexafin lutetium was used to assess the production of hydrogen peroxide under cell culture conditions following the protocol outlined in the previous example. NADPH alone had no inhibitory effect at concentrations at or below 1000 $\mu$M in the absence of motexafin lutetium, whereas a dose-response was observed towards motexafin lutetium at this concentration and at 333 $\mu$M. No inhibitory effect was seen at lower concentrations of NADPH. Motexafin lutetium had no inhibitory effect in the absence of NADPH.

Figure 12:
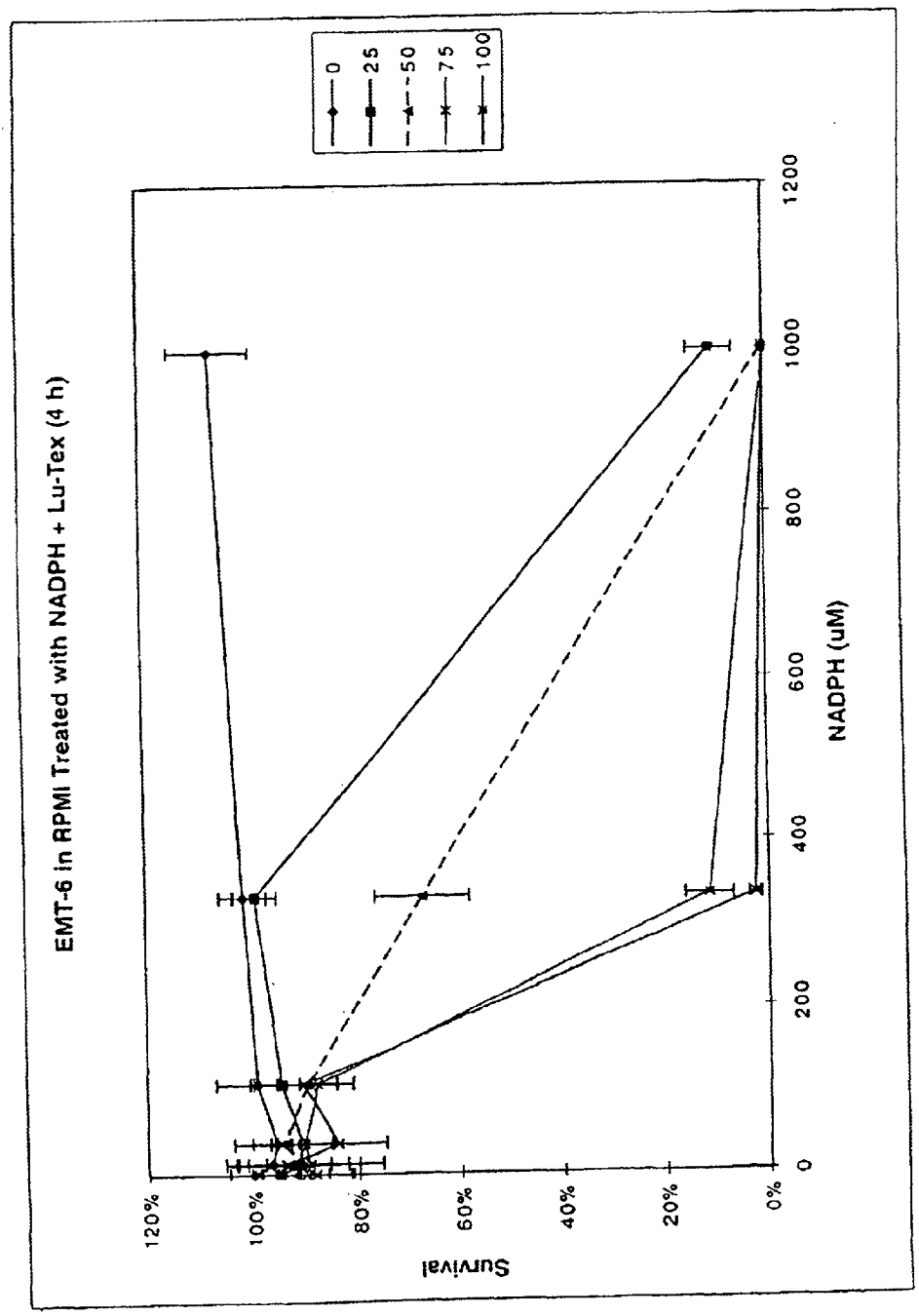
FIG. 12 illustrates the percent survival of EMT-6 mouse mammary sarcoma cells in the presence of varying concentrations of NADPH and varying concentrations of LuTex.

The results of this analysis are illustrated in FIG. 12. The toxicity of cells to the combination of sufficient concentrations of motexafin lutetium and NADPH is attributed to the production of toxic quantities of hydrogen peroxide and suggests probable radiation sensitization activity for motexafin lutetium.

Example 8

Production of $H_2O_2$ by the Gadolinium(III) Complex of Texaphyrin in the Presence of NADPH under Cell Culture Conditions The proliferation of EMT6 mouse mammary sarcoma (Rockwell, S. C., et al., *J. Natl. Cancer Inst.* 1972, 49, 735–749) cells grown in RPMI-1640 medium in the presence of NADPH and GdTex was used to assess the production of hydrogen peroxide under cell culture conditions following the protocol outlined in the previous example. NADPH alone had no inhibitory effect at concentrations at or below 1000 $\mu$M in the absence of GdTex, whereas a dose-response was observed towards GdTex at this concentration and at 333 $\mu$M. No inhibitory effect was seen at lower concentrations of NADPH. GdTex had no inhibitory effect in the absence of NADPH.

Figure 13:
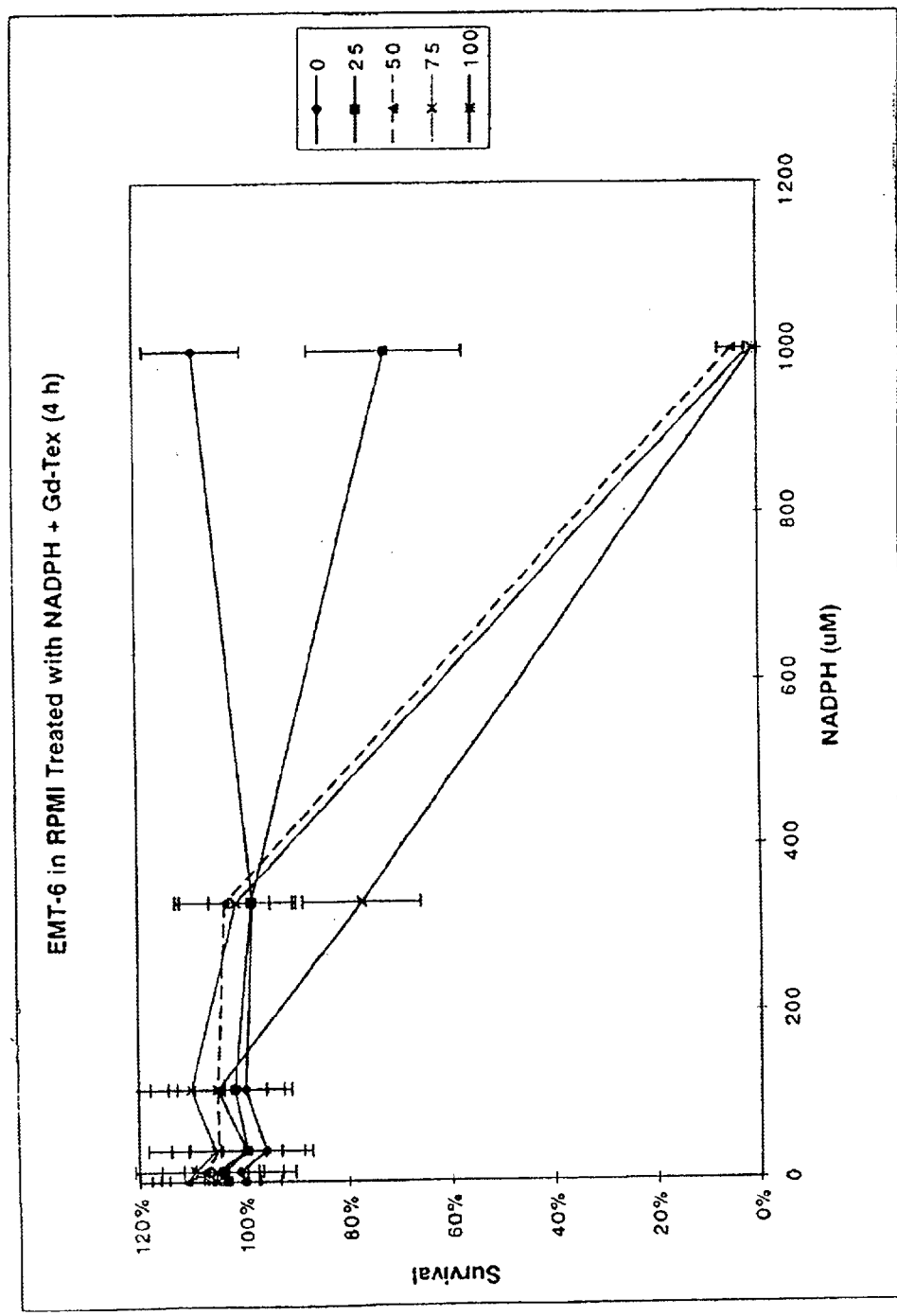
FIG. 13 illustrates the percent survival of EMT-6 mouse mammary sarcoma cells in the presence of varying concentrations of NADPH and varying concentrations of GdTex.

The results of this analysis are illustrated in FIG. 13. The toxicity of cells to the combination of sufficient concentrations of GdTex and NAD(P)H is attributed to the production of toxic quantities of hydrogen peroxide and suggests that motexafin gadolinium has probable radiation sensitization activity, albeit less than that of motexafin lutetium in a NADPH dominated metabolic pathway.

Example 9

The Cytotoxic Effect of L-Buthionine-[S,R]-Sulfoximine (BSO) in the presence of the Gadolinium(III) Complex of Texaphyrin under Cell Culture Conditions The proliferation of MES-SA human uterine cells grown in McCoys 5A medium in the presence of a thiol depleting agent (BSO) or GdTex was used to assess the combined effect of these agents. The protocol outlined in the previous example was followed, with the following changes:

1. The serially diluted compound was 200 $\mu$M BSO (Sigma Chemical, St. Louis, Mo., catalogue no. G1404).

2. The cells were allowed to incubate in the presence of the two drugs for ca. 72 hours, prior to exchange of media and analysis using the calorimetric (MTT) assay, as described, e.g., in Example 5.

GdTex had an inhibitory effect of ca. 50% in the absence of BSO. For clarity, the data has been normalized to discount the cytotoxic effect of GdTex alone. BSO alone had an inhibitory effect in the absence of GdTex of about 10% at the highest (50 $\mu$M) concentration tested. In the presence of increasing amounts of GdTex, an increase in the cytotoxic dose response of the cells towards BSO is seen. This indicates that cooperative cell growth inhibition occurs in the presence of the two agents.

Figure 14:
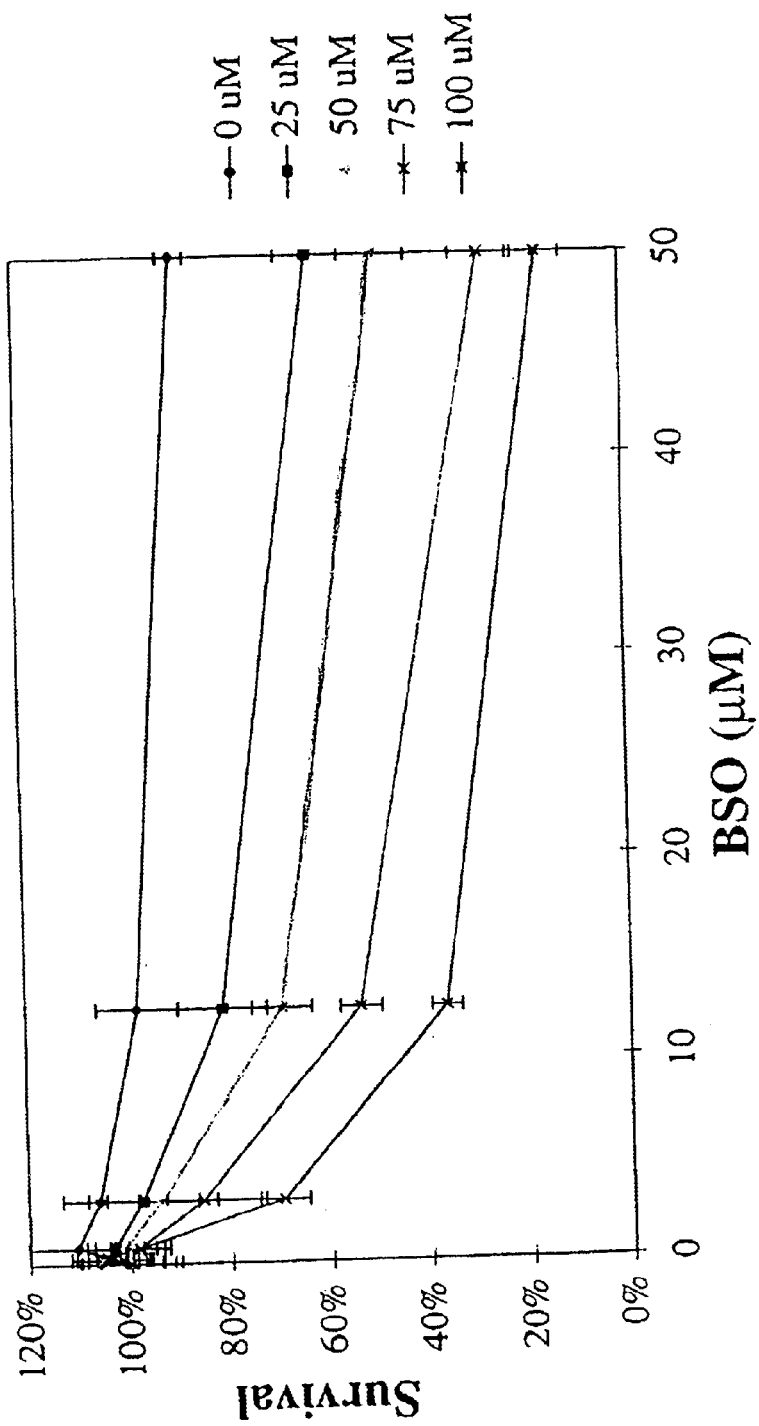
FIG. 14 illustrates the percent survival of MES-SA human uterine cells in the presence of varying concentrations of GdTex and BSO.

The results of this example are illustrated in FIG. 14.

Example 10

The Cytotoxic Effect of the Gadolinium(III) Complex of Texaphyrin and Ionizing Radiation, with and without L-Buthionine-[S,R]-Sulfoximine (BSO) under Cell Culture Conditions The response of ME-SA cells to ionizing radiation was studied using the microtiter plate format to confirm radiation sensitization potential. This assay is used to assess rapidly the effects of irradiation under a variety of conditions.

10A. Materials and Methods

MES-SA cells were incubated at 37° C. and allowed to adhere to 96-well microtiter plates (1000 cells per well) overnight in 160 $\mu$L McCoys 5A containing 10% FBS (Gibco-BRL) and ca. 2% penicillin/streptomycin solution (Sigma). BSO or media (20 $\mu$L) was added, respectively to test and control wells, 24 h prior to irradiation. Metallotexaphyrin complex (up to 100 $\mu$M) was added to the test wells to give a final volume of 200 $\mu$L, 18–24 h prior to irradiation. Plates were irradiated using a 137Cs irradiator (Model 40 Gammaceii, J. L. Shepherd & Assoc., San Fernando, Calif.) at a dose rate of 33.25 Rad/min. A lead brick (2" diameter) was positioned to protect a column of wells (no. 11) from ionizing radiation. Plate absorbances were normalized to shielded wells to allow plate-to-plate comparison. Control experiments demonstrated that data from columns 1–9 were not effected by shielding. Reversing the position of texaphyrin complex-containing wells had no effect on assay outcome. Medium was exchanged immediately after irradiation, and plates were incubated an additional 120 h prior to analysis for viability using the MTT assay (as described, e.g., in Example 5).

Results

Figure 17A:
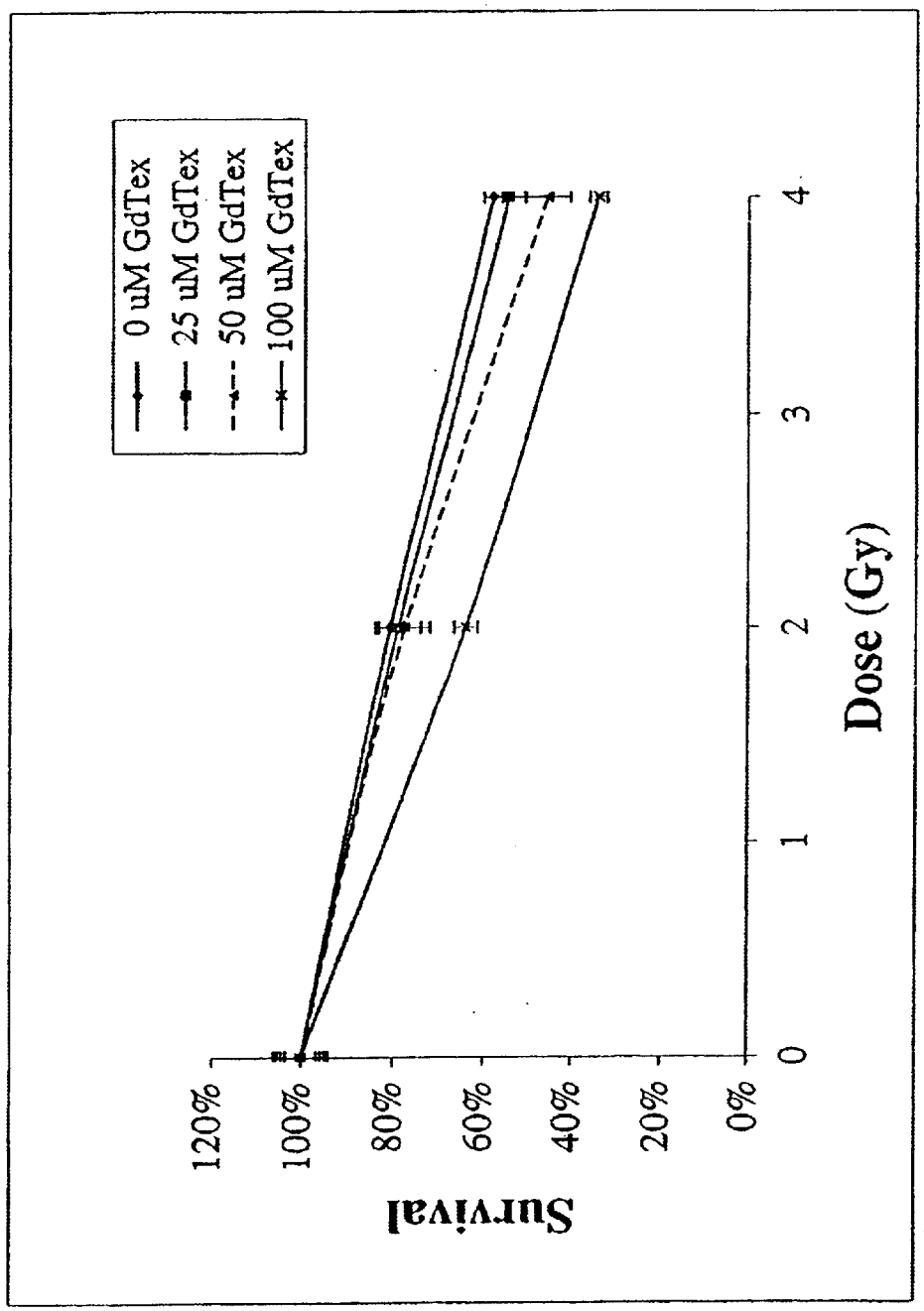
FIGS. 17A and 17B illustrates the percent survival of MES-SA human uterine cells with ionizing radiation and varying concentrations of GdTex, in the absence and the presence of BSO, respectively.
Figure 17B:
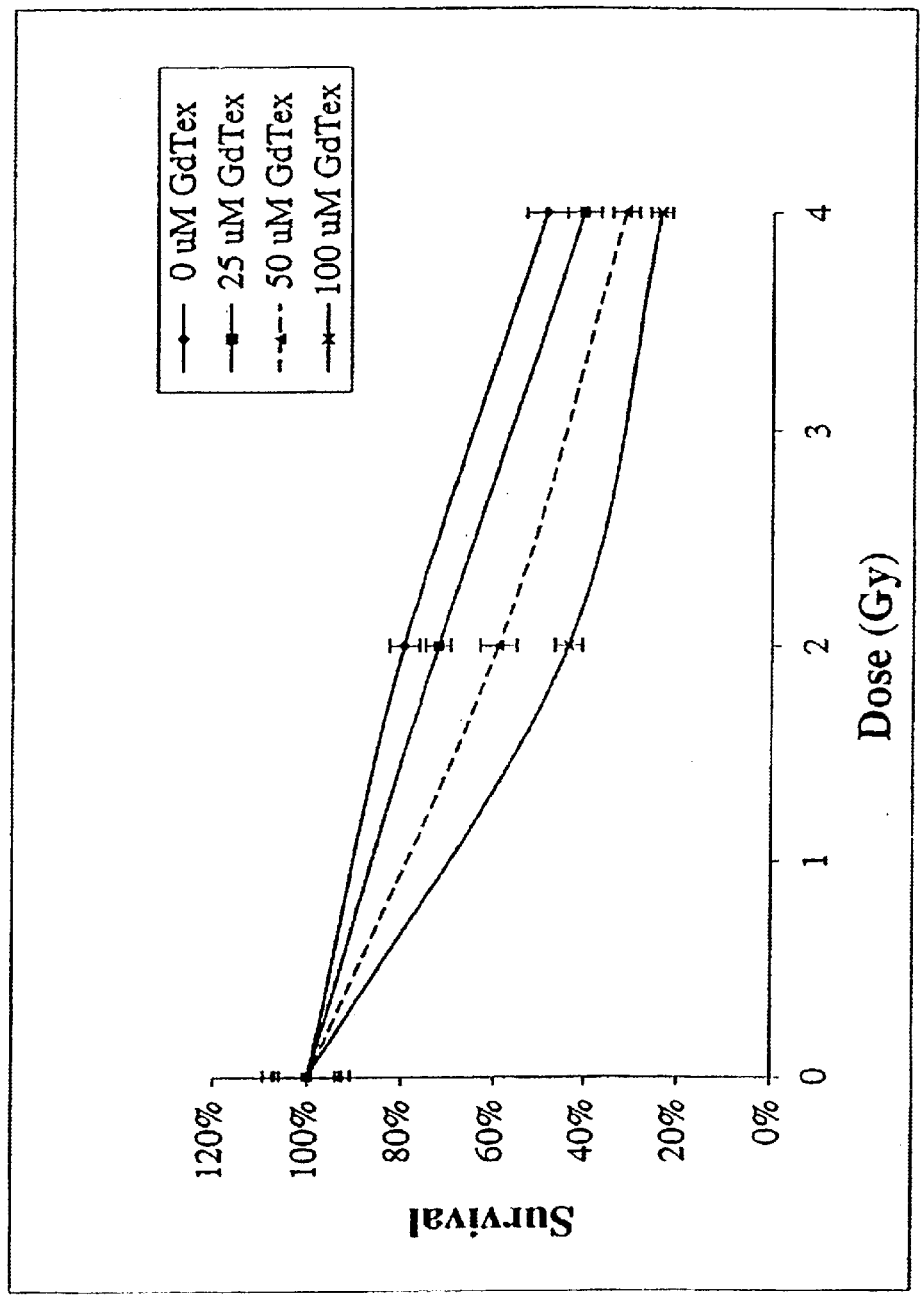

Treatment of MES-SA cells with up to 50 $\mu$M GdTex for 24 h prior to irradiation had a small effect on apparent viability, after adjustment for the effect of GdTex alone (FIG. 17A). Radiation sensitization became more significant at the 100 $\mu$M GdTex concentration. In the parallel experiment in which all cells were pre-incubated with 100 $\mu$M BSO, a greater GdTex-dependent decrease in apparent viability was observed (FIG. 17B). The effect of BSO appeared to be dose-dependent from 0 to 100 $\mu$M, and leveled off at higher BSO concentrations (data not shown).

These results corroborate the correlation between radiation sensitization potential and reactive oxygen species production from a cellular metabolite having a standard biochemical reduction potential more negative than the standard biochemical reduction of oxygen/hydrogen peroxide. Additionally, these results indicate that the radiation sensitization potential of GdTex, and presumably of other reactive oxygen species-producing sensitizers, can be augmented by co-administration of a thiol-depleting agent or other agents that interfere with cellular metabolic pathways.

10B. In corresponding experiments sensitization was not obtained when LuTex was substituted for GdTex, or when RPMI prepared with dialyzed serum (an ascorbate-free medium) was substituted for McCoys 5A with normal serum (an ascorbate containing medium).

Example 11

Radiation Sensitization as Determined by Clonogenic Assay

The response of MES-SA cells to ionizing radiation was studied using a clonogenic assay format to confirm radiation sensitization potential.

Materials and Methods

MES-SA cells (200 to 5,000 cells per dish) were plated in T-25 flasks in 8.5 mL McCoys 5A containing 10% FBS (Gibco-BRL) and ca. 2% penicillin/streptomycin solution (Sigma) and incubated at 37° C. overnight. Stock BSO, ascorbate, GdTex (or a control 5% mannitol) solutions were prepared and 0.5 mL of each added to each flask to give a final volume of 10 mL (final concentrations of BSO, ascorbate and GdTex were 100 $\mu$M, 5 $\mu$M and 50 $\mu$M, respectively) and the cells incubated for 24 hr, whereupon the flasks were irradiated using a 137Cs irradiator (Model 40 Gammacell, J. L. Shepherd & Assoc., San Fernando, Calif.) at a dose rate of 0.805 Gy/min. Medium was removed immediately after irradiation, the cells were washed with fresh medium (5.0 mL) followed by the addition of fresh medium (10 mL) and incubation for an additional 11 days. Colonies were fixed and stained with 1% crystal violet and then counted.

Results

As illustrated in FIG. 18, treatment of MES-SA cells with either 50 $\mu$M GdTex or 100 $\mu$M BSO for 24 h prior to irradiation had a relatively small effect on clonogenic survival as a function of radiation. Co-administration of 50 $\mu$M GdTex and 100 $\mu$M BSO resulted in a radiation response significantly greater than the sum of the responses obtained from them individually.

These results demonstrate that sensitization of the effects of ionizing radiation by GdTex can be confirmed in a clonogenic assay using ascorbate-containing medium, and that the co-administration of GdTex and BSO synergistically enhances the effects of ionizing radiation.

Example 12

The Cytotoxic Effect of Antimycins A and the Gadolinium (III) Complex of Texaphyrin under Cell Culture Conditions The proliferation of MES-SA human uterine cells grown in McCoys 5A medium in the presence of the thiol depleting agent BSO, with varying concentrations of a mitochondrial inhibitor (Antimycins A) and GdTex was used to assess the combined effect of these agents.

Materials and Methods

MES-SA cells were incubated at 37° C. and allowed to adhere to 96-well microtiter plates (2000 cells per well) overnight in 180 $\mu$L McCoys 5A containing 10% FBS (Gibco-BRL) and ca. 2% penicillin/streptomycin solution (Sigma). BSO (20 $\mu$L) was added to all wells followed by incubation for a further 24 h. The medium was exchanged and Antimycins A was serially diluted at concentrations ranging from 0 to 20 $\mu$M and after 0.5 hr metallotexaphyrin complex (up to 100 $\mu$M) was added to the test wells to give a final volume of 200 $\mu$L, followed by incubation for 20 h, whereupon the medium was exchanged and the plates were incubated an additional 52 h prior to analysis for viability using the MTT assay.

Results

In the presence of increasing amounts of GdTex, an increase in the cytotoxic dose response of the cells towards Antimycins A is seen. This indicates that cooperative cell growth inhibition occurs in the presence of the two agents. The results of this example are illustrated in FIG. 19.

From the foregoing description, various modifications and changes in the composition and method will occur to those skilled in the art. All such modifications coming within the scope of the appended claims are intended to be included therein.

What is claimed is:

1. A method of inducing targeted oxidative stress, in the absence of ionizing radiation, in cells in a mammalian host bearing a tumor or atheroma or other neoplastic tissue, which method comprises:

a) administering to said mammalian host a metal containing texaphyrin of Formula I

I 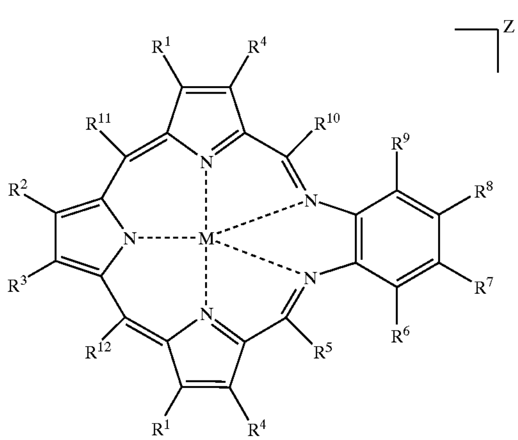 wherein M is a divalent metal cation or a trivalent metal cation;

$R^1$ to $R^4$ as well as $R^7$ and $R^8$ are independently selected from the group consisting of hydrogen, carboxyl, carboxylalkyl, acyl, acylamino, aminoacyl, alkyl, substituted alky (particularly hydroxyalkyl or aminoalkyl, and especially where $R^1$ is hydroxypropyl or aminopropyl), alkenyl, substituted alkenyl, alkoxy, substituted alkoxy, aryl, heteroaryl, heterocyclic, halo, hydroxyl, nitro, and a saccharide;

$R^6$ and $R^9$ are independently selected from the group consisting of hydrogen, carboxyl, carboxylalkyl, acyl, acylamino, aminoacyl, alkyl, substituted alkyl other than iodoalkyl, alkenyl, substituted alkenyl, alkoxy, substituted alkoxy, aryl, heteroaryl, heterocyclic, halo other than iodo, hydroxyl, nitro, and a saccharide;

$R^5$ and $R^{10}$ to $R^{12}$ are independently selected from the group consisting of hydrogen, alkyl, substituted alkyl, alkoxy, substituted alkoxy, carboxyl, carboxylalkyl, acyl and acylamino; and the charge, Z, is an integer having a value less than or equal to 5, that preferentially accumulates in tumor or atheroma or other neoplastic tissue cells and catalyzes the production of one or more reactive oxygen species from a cellular metabolite having a reduction potential more negative than that of molecular oxygen;

b) optionally, allowing sufficient time for said agent to preferentially accumulate in the cells of the tumor, atheroma or other neoplastic tissue; and c) administering to said mammalian host a cellular metabolite such as to increase the reactive oxygen species production in the tumor or atheroma or other neoplastic tissue.

2. The method of claim 1 wherein the reactive oxygen species is catalyzed from ascorbate and ascorbate is administered to said mammalian host.

3. The method of claim 1 wherein the reactive oxygen species is catalyzed from NAD(P)H and NAD(P)H is administered to said mammalian host.

4. A method of inducing targeted oxidative stress in cells in a mammalian host bearing a tumor or atheroma or other neoplastic tissue, which method comprises:

a) administering to said mammalian host an agent, wherein said agent is motexafin gadolium or motexafin lutetium or mixtures thereof, that preferentially accumulates in tumor or atheroma or other neoplastic tissue cells and catalyzes the production of one or more reactive oxygen species from a cellular metabolite;

b) optionally, allowing sufficient time for said agent to preferentially accumulate in the cells of the tumor, atheroma or other neoplastic tissue; and c) administering to said mammalian host a cellular metabolite such as to increase the reactive oxygen species production in the tumor or atheroma or other neoplastic tissue wherein the reactive oxygen species is catalyzed from ascorbate and ascorbate is administered to said mammalian host.

5. A method of inducing targeted oxidative stress, in cells in a mammalian host bearing a tumor or atheroma or other neoplastic tissue, which method comprises:

a) administering to said mammalian host an agent selected from motexafin gadolinium, motexafin lutetium or mixtures thereof, that preferentially accumulate in tumor or atheroma or other neoplastic tissue cells and catalyzes the production of one or more reactive oxygen species from a cellular metabolite b) optionally, allowing sufficient time for said agent to preferentially accumulate in the cells of the tumor, atheroma or other neoplastic tissue; and c) administering to said mammalian host a cellular metabolite such as to increase the reactive oxygen species production in the tumor or atheroma or other neoplastic tissue.

* * * * *